(12) United States Patent
Braun et al.

(10) Patent No.: US 6,645,984 B2
(45) Date of Patent: Nov. 11, 2003

(54) ARYLISOXAZOLINE DERIVATIVES, PROCESSES FOR THEIR PREPARATION AND THEIR USE AS PESTICIDES

(75) Inventors: Ralf Braun, Ramberg (DE); Oswald Ort, Glashütten (DE); Karl-Josef Haack, Niedernhausen (DE); Matthias Eckhardt, Biberach (DE); Waltraud Hempel, Liederbach (DE); Maria-Theresia Thönessen, Heidesheim (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 10/102,789

(22) Filed: Mar. 22, 2002

(65) Prior Publication Data
US 2003/0114501 A1 Jun. 19, 2003

(30) Foreign Application Priority Data

Mar. 23, 2001 (DE) .......................... 101 14 597

(51) Int. Cl.$^7$ .................... A01N 43/40; A01N 43/80; A01N 43/76; C07D 413/14; C07D 413/10
(52) U.S. Cl. .................... 514/326; 548/237; 546/269.1; 546/211; 546/208; 504/100; 504/244; 504/248; 504/270; 514/357; 514/374
(58) Field of Search .................... 548/237; 504/100, 504/248, 270, 244; 514/326, 357, 374; 546/211, 208, 269.1

(56) References Cited

FOREIGN PATENT DOCUMENTS

| EP | 0174695 A2 | 3/1986 |
| EP | 0611760 A1 | 8/1994 |
| US | WO 93/24470 | * 12/1993 |
| WO | WO 93/24470 A1 | 12/1993 |
| WO | WO 95/04726 A1 | 2/1995 |
| WO | WO 96/22283 A1 | 7/1996 |

* cited by examiner

*Primary Examiner*—Joseph K. McKane
*Assistant Examiner*—Rebecca Anderson
(74) *Attorney, Agent, or Firm*—Burns, Doane, Swecker & Mathis, L.L.P.

(57) ABSTRACT

Compounds of the formula (I),

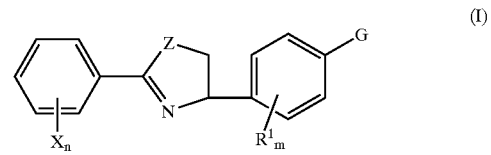

are described in which

X is halogen, cyano, nitro, $(C_1-C_4)$-alkyl, $(C_1-C_4)$-alkoxy, $(C_1-C_4)$-alkylthio or $(C_1-C_4)$-alkylsulfinyl;

$R^1$ is halogen, $(C_1-C_4)$-haloalkyl, $(C_1-C_4)$-alkyl, $(C_1-C_4)$-alkoxy, $(C_1-C_4)$-haloalkoxy or cyano;

m is 0 to 3;

n is 1 to 5;

Z is oxygen, sulfur, $CH_2$ or $NR^2$;

$R^2$ is CN, $(C_1-C_4)$-alkoxy-$(C_1-C_4)$-alkyl, CHO, $(C_1-C_6)$-alkylcarbonyl, $(C_1-C_6)$-alkoxycarbonyl or $(CW)NR^3R^4$;

$R^3$, $R^4$ are H or $(C_1-C_6)$-alkyl;

W is O or S;

G is mono- to tetrasubstituted isoxazoline which is attached in the 3-, 4- or 5-position to the adjacent phenyl ring. The compounds are suitable for use as pesticides.

20 Claims, No Drawings

ARYLISOXAZOLINE DERIVATIVES, PROCESSES FOR THEIR PREPARATION AND THEIR USE AS PESTICIDES

BACKGROUND OF THE INVENTION

Arylisoxazoline derivatives, processes for their preparation and their use as pesticides The invention relates to arylisoxazoline derivatives, to processes for their preparation, to compositions comprising them and to their use for controlling animal pests, in particular arthropods, such as insects and Acarina, and helminths.

DESCRIPTION OF THE INVENTION

Owing to their biological activity, certain 1,3-oxazolines, 1,3-thiazolines, pyrrolines and imidazolines are suitable for controlling animal pests (see, for example, WO-A-93/24470, WO-A-95/04726 and WO-A-96/22283).

However, owing to the multifarious requirements that modem pesticides have to meet, for example with respect to efficacy, persistency, activity spectrum, use spectrum, toxicity, combination with other active compounds, combination with formulating agents or synthesis, and owing to the possible occurrence of resistance, the development of such substances can never be considered to be concluded, and there is a constant great need for novel compounds which, at least in some aspects, offer advantages compared to the known compounds.

It was an object of the present invention to provide compounds which, under various aspects, widen the spectrum of pesticides.

SUMMARY OF THE INVENTION

This object and other objects which have not been explicitly mentioned, which can be derived or deduced from the contexts discussed here, are achieved by arylisoxazoline derivatives of the formula (I),

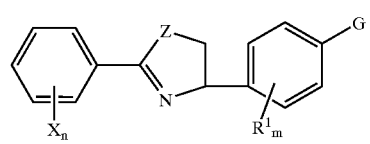

(I)

in which the symbols and indices are as defined below:

X is identical or different
  a) halogen, cyano, nitro;
  b) $(C_1-C_4)$-alkyl, $(C_1-C_4)$-alkoxy, $(C_1-C_4)$-alkylthio, $(C_1-C_4)$-alkylsulfinyl, where the radicals of group b are unsubstituted or substituted by one or more, preferably one, two or three, radicals selected from the group consisting of halogen;

$R^1$ is identical or different halogen, $(C_1-C_4)$-haloalkyl, $(C_1-C_4)$-alkyl, $(C_1-C_4)$-alkoxy, $(C_1-C_4)$-haloalkoxy or cyano;

m is 0, 1, 2, 3 or 4;
n is 1, 2, 3, 4 or 5;
Z is oxygen, sulfur, $CH_2$ or $NR^2$;
  $R^2$ is CN, $(C_1-C_4)$-alkoxy-$(C_1-C_4)$-alkyl, CHO, $(C_1-C_6)$-alkylcarbonyl, $(C_1-C_6)$-alkoxycarbonyl or $(CW)NR^3R^4$;

$R^3$, $R^4$ are identical or different H, $(C_1-C_6)$-alkyl;
W is O or S;
G is mono- to tetrasubstituted, preferably mono- or disubstituted, isoxazoline which is attached in the 3-, 4- or 5-position to the adjacent phenyl ring;
their pure isomers (optical and geometrical isomers), isomer mixtures, N-oxides and salts suitable for use as pesticides.

Surprisingly, compounds of the formula (I) have, with respect to the activity spectrum and the potency, better acaricidal and insecticidal action than known 1,3-oxazoline, 1,3-thiazoline, pyrroline or imidazoline derivatives.

DESCRIPTION OF PREFERRED EMBODIMENTS

The symbols and indices in formula (I) preferably have the following meanings:

X is preferably halogen, in particular Cl, Br or F, cyano, nitro, $(C_1-C_4)$-alkyl, $(C_1-C_3)$-haloalkyl, $(C_1-C_4)$-alkoxy or $(C_1-C_3)$-haloalkoxy.

X is particularly preferably halogen, in particular Cl, Br or F, $(C_1-C_4)$-alkyl, $(C_1-C_3)$-haloalkyl, $(C_1-C_4)$-alkoxy or $(C_1-C_3)$-haloalkoxy.

m is preferably 0 or 1.
n is preferably 1, 2 or 3.
Z is preferably oxygen or $CH_2$.
$R^1$ is preferably H, halogen, $(C_1-C_4)$-haloalkyl, $(C_1-C_4)$-alkyl, $(C_1-C_4)$-alkoxy, $(C_1-C_4)$-haloalkoxy.
G is preferably

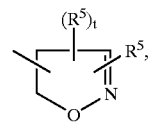

particularly preferably

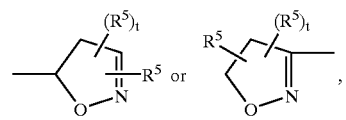

very particularly preferably

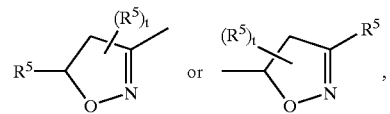

in particular

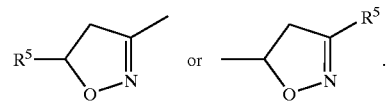

t is 0, 1, 2 or 3, preferably 0 or 1.
$R^5$ is identical or different
  a) halogen, CN, $NO_2$;
  b) a straight-chain or branched alkyl group having 1 to 12 carbon atoms, where one or more $(CH_2)$ groups are optionally replaced by —O—, —S(O)—$_{0,1,2}$, —NH—, —$NR^6$—, —CO—, —CS—, —CH=CH—, —C≡C—, unsubstituted or substituted aryldiyl, unsubstituted or substituted heterocyclyldiyl, unsubstituted or substituted $(C_3-C_8)$-cycloalkanediyl or unsubstituted or substituted $(C_3-C_8)$-cycloalkenediyl, with the proviso that chalcogens may not be adjacent to one another, where two radicals $R^5$ together with the atoms of the isoxazoline ring optionally form a 3- to 8-membered ring system and where individual hydrogen atoms are optionally replaced by halogen;

c) in the case of two radicals $R^5$ located in the α-position, the radicals are also (=Y), where Y is (=O), (=S), (=NOR$^6$) or (=CR$_2^6$);

with the proviso that the radical(s) $R^5$ together do not comprise more than one ring system having five or more members.

$R^6$ is $(C_1-C_4)$-alkyl, unsubstituted or substituted phenyl or unsubstituted or substituted benzyl.

As substituents on the isoxazoline radical, the radicals $R^5$ preferably have the following meanings:

$R^5$ is identical or different D-$R^7$, or two radicals $R^5$ together with the atoms to which they are attached form a three to eight-membered saturated or unsaturated ring system which is unsubstituted or substituted by one or more radicals $R^7$ and which optionally also contains further heteroatoms, preferably O, N, S, SO and/or $SO_2$;

D is a direct bond or $(C_1-C_6)$-alkanediyl, unsubstituted or substituted by one or more halogen atoms;

$R^7$ is identical or different $R^8$, $R^9$, —C(W)$R^8$, —C(=NOR$^8$)$R^8$, —C(=NNR$^8_2$)$R^8$, —C(=W)OR$^8$, —C(=W)NR$^8_2$, —OC(=W)R$^8$, —OC(=W)OR$^8$, —NR$^8$C(=W)R$^8$, —N[C(=W)R$^8$]$_2$, —NR$^8$C(=W)OR$^8$, —C(=W)NR$^8$—NR$^8_2$, —C(=W)NR$^8$—NR$^8$[C(=W)R$^8$], —NR$^8$—C(=W)NR$^8_2$, —NR$^8$—NR$^8$C(=W)R$^8$, —NR$^8$—N[C(=W)R$^8$]$_2$, —N[(C=W)R$^8$]—NR$^8_2$, —NR$^8$—N[(C=W)WR$^8$], —NR$^8$[(C=W)NR$^8_2$], —NR$^8$(C=NR$^8$)R$^8$, —NR$^8$(C=NR$^8$)NR$^8_2$, —O—NR$^8_2$, —O—NR$^8$(C=W)R$^8$, —SO$_2$NR$^8_2$, —NR$^8$SO$_2$R$^8$, —SO$_2$OR$^8$, —OSO$_2$R$^8$, —OR$^8$, —NR$^8_2$, —SR$^8$, —SiR$^8_3$, —PR$^8_2$, —P(=W)R$^8_2$, —SOR$^8$, —SO$_2$R$^8$, —PW$_2$R$^8_2$, —PW$_3$R$^8_2$ or two radicals $R^7$ together are (=Y), (=N—$R^8$), (=CR$_2^8$) or (=CHR$^8$);

W is O or S;

$R^8$ is identical or different H, $(C_1-C_6)$-alkyl, $(C_2-C_6)$-alkenyl, $(C_2-C_6)$-alkynyl, $(C_3-C_8)$-cycloalkyl, $(C_4-C_8)$-cycloalkenyl, $(C_3-C_8)$-cycloalkyl-$(C_1-C_4)$-alkyl, $(C_4-C_8)$-cycloalkenyl-$(C_1-C_4)$-alkyl, $(C_3-C_8)$-cycloalkyl-$(C_2-C_4)$-alkenyl, $(C_4-C_8)$-cycloalkenyl-$(C_2-C_4)$-alkenyl, $(C_1-C_8)$-alkyl-$(C_3-C_8)$-cycloalkyl, $(C_2-C_6)$-alkenyl-$(C_3-C_8)$-cycloalkyl, $(C_2-C_6)$-alkynyl-$(C_3-C_8)$-cycloalkyl, $(C_1-C_6)$-alkyl-$(C_4-C_8)$-cycloalkenyl, $(C_2-C_6)$-alkenyl-$(C_4-C_8)$-cycloalkenyl, aryl, heterocyclyl; where the radicals mentioned are unsubstituted or substituted by one or more radicals $R^9$ and optionally two radicals $R^8$ together form a ring system;

$R^9$ is identical or different halogen, cyano, nitro, hydroxyl, thio, amino, $(C_1-C_8)$-alkanoyl, $(C_2-C_6)$-haloalkanoyl, $(C_1-C_6)$-alkoxy, $(C_3-C_6)$-alkenyloxy, $(C_3-C_6)$-alkynyloxy, $(C_1-C_6)$-haloalkoxy, $(C_3-C_6)$-haloalkenyloxy, $(C_3-C_6)$-haloalkynyloxy, $(C_3-C_8)$-cycloalkoxy, $(C_4-C_8)$-cycloalkenyloxy, $(C_3-C_8)$-halocycloalkoxy, $(C_4-C_8)$-halocycloalkenyloxy, $(C_3-C_8)$-cycloalkyl-$(C_1-C_4)$-alkoxy, $(C_4-C_8)$-cycloalkenyl-$(C_1-C_4)$-alkoxy, $(C_3-C_8)$-cycloalkyl-$(C_2-C_4)$-alkenyloxy, $(C_4-C_8)$-cycloalkenyl-$(C_1-C_4)$-alkenyloxy, $(C_1-C_6)$-alkyl-$(C_3-C_8)$-cycloalkoxy, $(C_2-C_6)$-alkenyl-$(C_3-C_8)$-cycloalkoxy, $(C_2-C_6)$-alkynyl-$(C_3-C_8)$-cycloalkoxy, $(C_1-C_6)$-alkyl-$(C_4-C_8)$-cycloalkenyloxy, $(C_2-C_6)$-alkenyl-$(C_4-C_8)$-cycloalkenyloxy, $(C_1-C_4)$-alkoxy-$(C_1-C_6)$-alkoxy, $(C_1-C_4)$-alkoxy-$(C_3-C_6)$-alkenyloxy, carbamoyl, $(C_1-C_6)$-mono- or dialkylcarbamoyl, $(C_1-C_6)$-mono- or dihaloalkylcarbamoyl, $(C_3-C_8)$-mono- or dicycloalkylcarbamoyl, $(C_1-C_6)$-alkoxycarbonyl, $(C_3-C_8)$-cycloalkoxycarbonyl, $(C_1-C_6)$-alkanoyloxy, $(C_3-C_8)$-cycloalkanoyloxy, $(C_1-C_6)$-haloalkoxycarbonyl, $(C_1-C_6)$-haloalkanoyloxy, $(C_1-C_6)$-alkaneamido, $(C_1-C_6)$-haloalkaneamido, C(O)NH$(C_1-C_6)$-alkyl, C(O)NH$(C_1-C_6)$-haloalkyl, C(O)N$[(C_1-C_6)$-alkyl$]_2$, C(O)N$[(C_1-C_6)$-haloalkyl$]_2$, $(C_2-C_6)$,alkeneamido, $(C_3-C_8)$-cycloalkaneamido, $(C_3-C_8)$-cycloalkyl-$(C_1-C_4)$-alkaneamido, $(C_1-C_6)$-alkylthio, $(C_3-C_6)$-alkenylthio, $(C_3-C_6)$-alkynylthio, $(C_1-C_6)$-haloalkylthio, $(C_3-C_6)$-haloalkenylthio, $(C_3-C_6)$-haloalkynylthio, $(C_3-C_8)$-cycloalkylthio, $(C_4-C_8)$-cycloalkenylthio, $(C_3-C_8)$-halocycloalkylthio, $(C_4-C_8)$-halocycloalkenylthio, $(C_3-C_8)$-cycloalkyl-$(C_1-C_4)$-alkylthio, $(C_4-C_8)$-cycloalkenyl-$(C_1-C_4)$-alkylthio, $(C_3-C_8)$-cycloalkyl-$(C_3-C_4)$-alkenylthio, $(C_4-C_8)$-cycloalkenyl-$(C_3-C_4)$-alkenylthio, $(C_1-C_6)$-alkyl-$(C_3-C_8)$-cycloalkylthio, $(C_2-C_6)$-alkenyl-$(C_3-C_8)$-cycloalkylthio, $(C_2-C_6)$-alkynyl-$(C_3-C_8)$-cycloalkylthio, $(C_1-C_6)$-alkyl-$(C_4-C_8)$-cycloalkenylthio, $(C_2-C_6)$-alkenyl-$(C_4-C_8)$-cycloalkenylthio, $(C_1-C_6)$-alkylsulfinyl, $(C_3-C_6)$-alkenylsulfinyl, $(C_3-C_6)$-alkynylsulfinyl, $(C_1-C_6)$-haloalkylsulfinyl, $(C_3-C_6)$-haloalkenylsulfinyl, $(C_3-C_6)$-haloalkynylsulfinyl, $(C_3-C_8)$-cycloalkylsulfinyl, $(C_4-C_8)$-cycloalkenylsulfinyl, $(C_3-C_8)$-halocycloalkylsulfinyl, $(C_4-C_8)$-halocycloalkenylsulfinyl, $(C_3-C_8)$-cycloalkyl-$(C_1-C_4)$-alkylsulfinyl, $(C_4-C_8)$-cycloalkenyl-$(C_1-C_4)$-alkylsulfinyl, $(C_3-C_8)$-cycloalkyl-$(C_3-C_4)$-alkenylsulfinyl, $(C_4-C_8)$-cycloalkenyl-$(C_3-C_4)$-alkenylsulfinyl, $(C_1-C_6)$-alkyl-$(C_3-C_8)$-cycloalkylsulfinyl, $(C_2-C_6)$-alkenyl-$(C_3-C_8)$-cycloalkylsulfinyl, $(C_2-C_6)$-alkynyl-$(C_3-C_8)$-cycloalkylsulfinyl, $(C_1-C_6)$-alkyl-$(C_4-C_8)$-cycloalkenylsulfinyl, $(C_2-C_6)$-alkenyl-$(C_4-C_8)$-cycloalkenylsulfinyl, $(C_1-C_6)$-alkylsulfonyl, $(C_3-C_6)$-alkenylsulfonyl, $(C_3-C_6)$-alkynylsulfonyl, $(C_1-C_6)$-haloalkylsulfonyl, $(C_3-C_6)$-haloalkenylsulfonyl, $(C_3-C_6)$-haloalkynylsulfonyl, $(C_3-C_8)$-cycloalkylsulfonyl, $(C_4-C_8)$-cycloalkenylsulfonyl, $(C_3-C_8)$-halocycloalkylsulfonyl, $(C_4-C_8)$-halocycloalkenylsulfonyl, $(C_3-C_8)$-cycloalkyl-$(C_1-C_4)$-alkylsulfonyl, $(C_4-C_8)$-cycloalkenyl-$(C_1-C_4)$-alkylsulfonyl, $(C_3-C_8)$-cycloalkyl-$(C_3-C_4)$-alkenylsulfonyl, $(C_4-C_8)$-cycloalkenyl-$(C_3-C_4)$-alkenylsulfonyl, $(C_1-C_6)$-alkyl-$(C_3-C_8)$-cycloalkylsulfonyl, $(C_2-C_6)$-alkenyl-$(C_3-C_8)$-cycloalkylsulfonyl, $(C_2-C_6)$-alkynyl-$(C_3-C_8)$-cycloalkylsulfonyl, $(C_1-C_6)$-alkyl-$(C_4-C_8)$-cycloalkenylsulfonyl, $(C_2-C_6)$-alkenyl-$(C_4-C_8)$-cycloalkenylsulfonyl, $(C_1-C_6)$-dialkylamino, $(C_1-C_6)$-alkylamino, $(C_3-C_6)$-alkenylamino, $(C_3-C_6)$-alkynylamino, $(C_1-C_6)$-haloalkylamino, $(C_3-C_6)$-haloalkenylamino, $(C_3-C_6)$-haloalkynylamino, $(C_3-C_8)$-cycloalkylamino, $(C_4-C_8)$-cycloalkenylamino, $(C_3-C_8)$-halocycloalkamino, $(C_4-C_8)$-halocycloalkenylamino, $(C_3-C_8)$-cycloalkyl- (C₁–C₄)-alkylamino, (C₄–C₈)-cycloalkenyl-(C₁–C₄)-alkylamino, (C₃–C₈)-cycloalkyl-(C₃–C₄)-alkenylamino, (C₄–C₈)-cycloalkenyl-(C₃–C₄)-alkenylamino, (C₁–C₆)-alkyl-(C₃–C₈)-cycloalkylamino, (C₂–C₆)-alkenyl-(C₃–C₈)-cycloalkylamino, (C₂–C₆)-alkynyl-(C₃–C₈)-cycloalkylamino, (C₁–C₆)-alkyl-(C₄–C₈)-cycloalkenylamino, (C₂–C₆)-alkenyl-(C₄–C₈)-cycloalkenylamino, (C₁–C₆)-trialkylsilyl, aryl, aryloxy, arylthio, arylamino, aryl-(C₁–C₄)-alkoxy, aryl-(C₁–C₆)-alkanoyl, aryl-(C₃–C₄)-alkenyloxy, aryl-(C₁–C₄)-alkylthio, aryl-(C₂–C₄)-alkenylthio, aryl-(C₁–C₄)-alkylamino, aryl-(C₃–C₄)-alkenylamino, aryl-(C₁–C₆)-dialkylsilyl, diaryl-(C₁–C₆)-alkylsilyl, triarylsilyl and 5- or 6-membered heterocyclyl, where the cyclic radicals are unsubstituted or substituted by one or more radicals selected from the group consisting of halogen, cyano, nitro, amino, hydroxyl, thio, (C₁–C₄)alkyl, (C₁–C₄)-haloalkyl, (C₃–C₈)-cycloalkyl, (C₁–C₄)-alkoxy, (C₁–C₄)-haloalkoxy, (C₁–C₄)-alkylthio, (C₁–C₄)-haloalkylthio, (C₁–C₄)-alkylamino, (C₁–C₄)-haloalkylamino and (C₁–C₄)-alkanoyl.

Particularly preferably,

R⁵ is CN, unsubstituted or substituted phenyl, unsubstituted or substituted phenoxy, (C₁–C₆)-alkyl, (C₁–C₆)-alkenyl, (C₁–C₆)-haloalkyl, (C₁–C₈)-haloalkenyl, —(C₁–C₆)-alkanediyl-aryl, where the aryl group is unsubstituted or substituted and where one —CH₂ unit is optionally replaced by —C(O)—NR¹⁰—, NR¹⁰—(CO), NR¹⁰ or O.

R¹⁰ is H, (C₁–C₆)-alkyl, (C₁–C₆)-haloalkyl, unsubstituted or substituted phenyl, unsubstituted or substituted benzyl.

Particularly preferred for

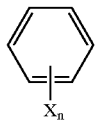

are the groups

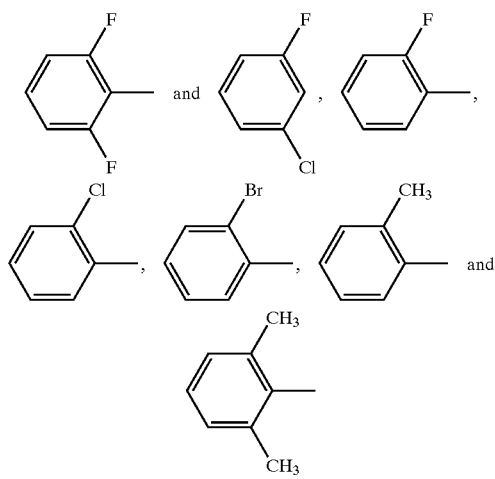

Particularly preferred groups of compounds of the formula (I) are those of the formulae (I1) to (I28):

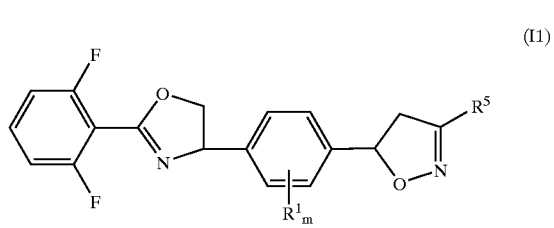
(I1)

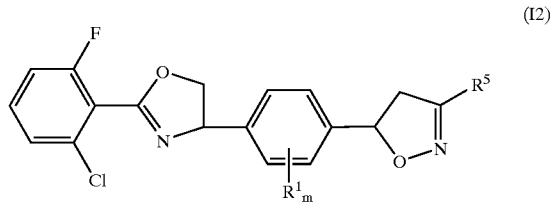
(I2)

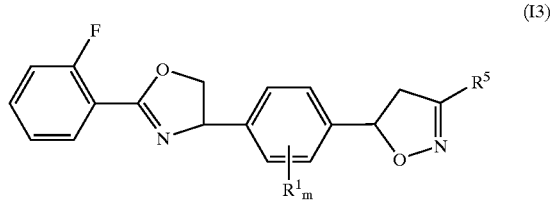
(I3)

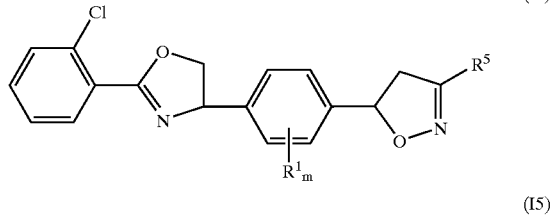
(I4)

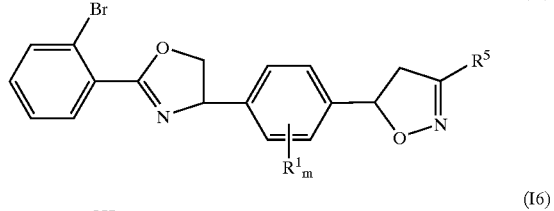
(I5)

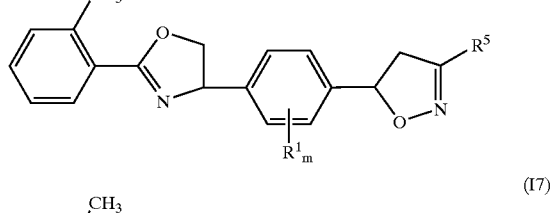
(I6)

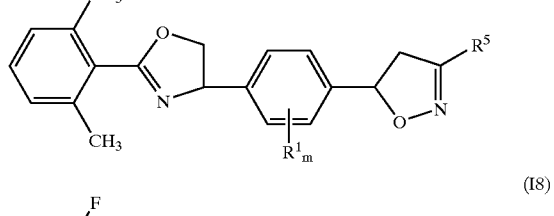
(I7)

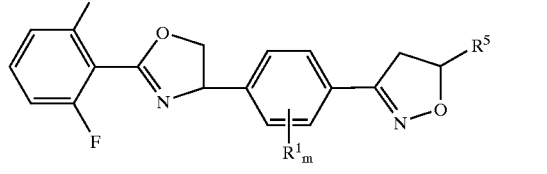
(I8)

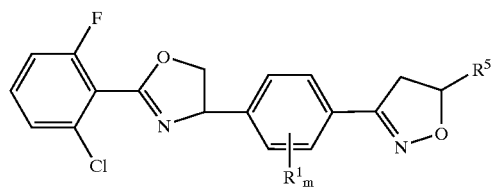
(I9)
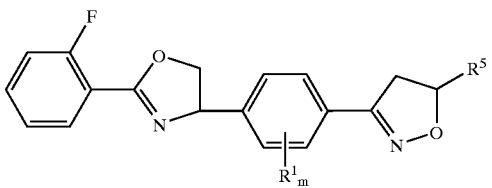
(I10)
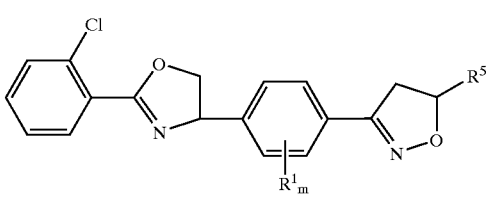
(I11)
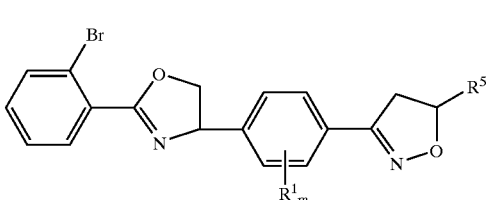
(I12)
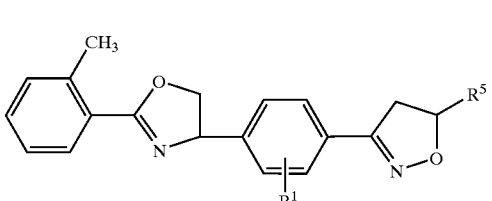
(I13)
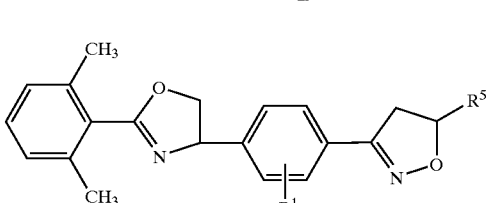
(I14)
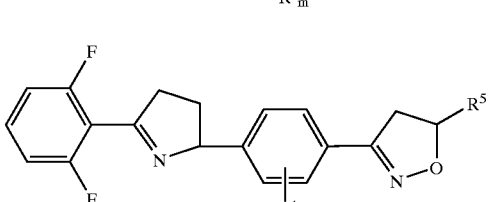
(I15)
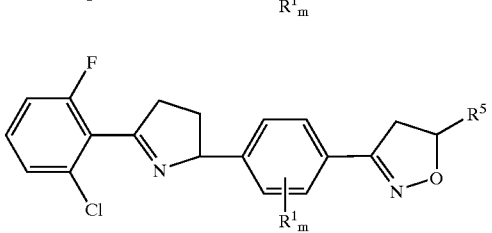
(I16)
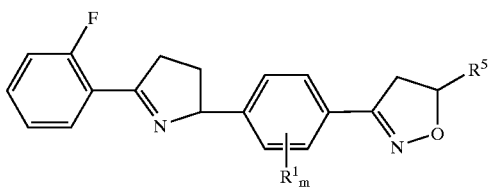
(I17)
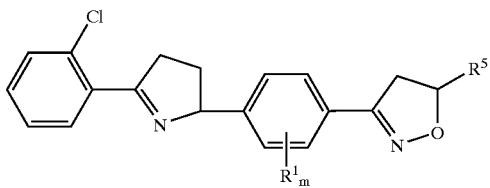
(I18)
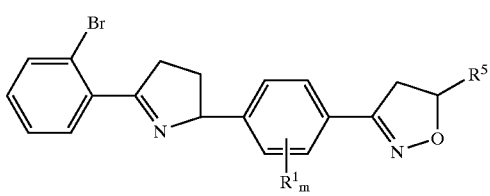
(I19)
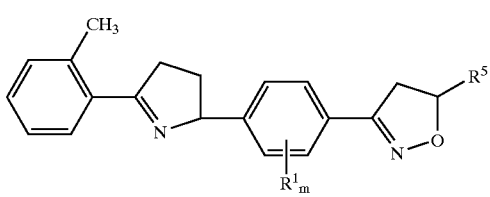
(I20)
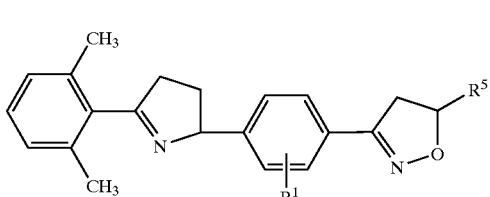
(I21)
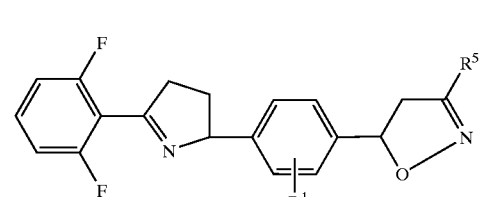
(I22)
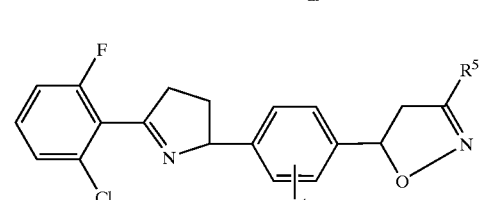
(I23)
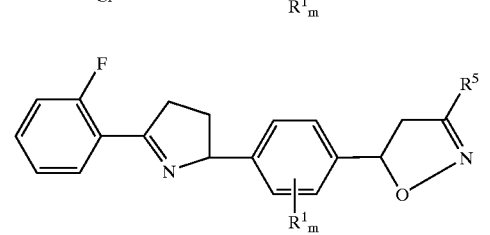
(I24)

-continued

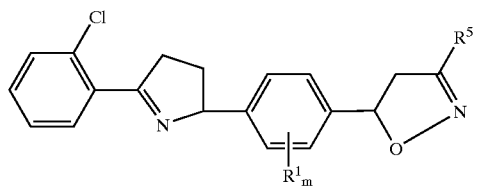

(I25)

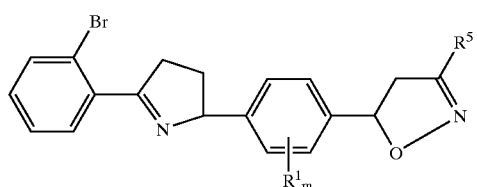

(I26)

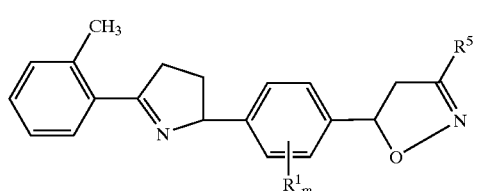

(I27)

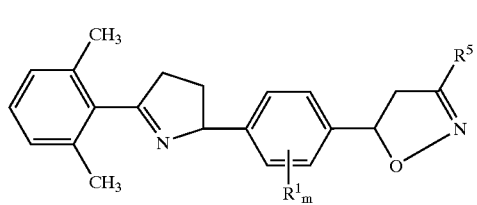

(I28)

In the above formula, "halogen" is to be understood as meaning a fluorine, chlorine, bromine or iodine atom;

the term "$(C_1-C_4)$-alkyl" is to be understood as meaning an unbranched or branched hydrocarbon radical having 1 to 4 carbon atoms, such as, for example, the methyl, ethyl, propyl, isopropyl, 1-butyl, 2-butyl, 2-methylpropyl or tert-butyl radical;

the term "$(C_1-C_6)$-alkyl" is to be understood as meaning the abovementioned alkyl radicals and also, for example, the pentyl, 2-methylbutyl, 1,1-dimethylpropyl or the hexyl radical;

the term "$(C_1-C_6)$-alkanediyl" is to be understood as meaning an unbranched or branched alkanediyl radical having 1 to 6 carbon atoms, such as methylene, ethane-1,2-diyl, propane-1,2-diyl, propane-1,3-diyl, butane-1,4-diyl, butane-1,3-diyl or 2-methylpropane-1,3-diyl;

the term "$(C_1-C_4)$-haloalkyl" is to be understood as meaning an alkyl group mentioned under the term "$(C_1-C_4)$-alkyl" in which one or more hydrogen atoms are replaced by the abovementioned halogen atoms, preferably chlorine or fluorine, such as, for example, the trifluoromethyl group, the 1-fluoroethyl group, the 2,2,2-trifluoroethyl group, the chloromethyl or fluoromethyl group, the difluoromethyl group or the 1,1,2,2-tetrafluoroethyl group;

the term "$(C_3-C_8)$-cycloalkyl" is to be understood as meaning, for example, the cyclopropyl, cyclobutyl or cyclopentyl group; and also the cyclohexyl, cycloheptyl or cyclooctyl radical;

the term "$(C_3-C_8)$-halocycloalkyl" is to be understood as meaning one of the $(C_3-C_8)$-cycloalkyl radicals listed above, in which one or more, in the case of fluorine optionally also all, hydrogen atoms are replaced by halogen, preferably fluorine or chlorine, such as, for example, the 2,2-difluoro- or 2,2-dichlorocyclopropane group or the fluorocyclopentane radical;

the term "$(C_2-C_4)$-alkenyl" is to be understood as meaning, for example, the vinyl, allyl, 2-methyl-2-propenyl or 2-butenyl group;

the term "$(C_2-C_4)$-haloalkenyl" is to be understood as meaning a $(C_2-C_4)$-alkenyl group in which some of, or in the case of fluorine also all, the hydrogen atoms are replaced by halogen, preferably fluorine or chlorine;

the term "$(C_2-C_4)$-alkynyl" is to be understood as meaning, for example, the ethynyl, propargyl, 2-methyl-2-propynyl or 2-butynyl group;

the term "$(C_2-C_6)$-alkynyl" is to be understood as meaning, for example, the abovementioned radicals and also, for example, the 1-pentynyl, 2-pentynyl, 3-pentynyl, or the 4-pentynyl group;

the term "haloalkynyl" is to be understood as meaning an alkynyl group in which some of, in the case of fluorine also all, the hydrogen atoms are replaced by halogen atoms, preferably fluorine or chlorine;

the term "$(C_1-C_4)$-alkanoyl-$(C_1-C_4)$-alkyl" is to be understood as meaning, for example, an acetylmethyl, propionylmethyl, 2-acetylethyl or a butyrylmethyl group;

the term "$(C_1-C_4)$-alkanoyl" is to be understood as meaning, for example, the formyl, acetyl, propionyl, 2-methylpropionyl or butyryl group;

the term "$(C_1-C_6)$-alkanoyl" is to be understood as meaning the abovementioned radicals and also, for example, the valeroyl, pivaloyl or hexanoyl group;

the term "$(C_2-C_6)$-haloalkanoyl" is to be understood as meaning a $(C_2-C_6)$-alkanoyl group in which some of, in the case of fluorine also all, the hydrogen atoms are replaced by halogen atoms, preferably fluorine or chlorine;

the term "$(C_1-C_6)$-alkoxycarbonyl" is to be understood as meaning, for example, the methoxycarbonyl, ethoxycarbonyl, propoxycarbonyl, butoxycarbonyl, tert-butoxycarbonyl, pentyloxycarbonyl or hexyloxycarbonyl group;

the term "$(C_1-C_6)$-haloalkoxycarbonyl" is to be understood as meaning a $(C_1-C_6)$-alkoxycarbonyl group in which one or more, in the case of fluorine optionally also all, hydrogen atoms are replaced by halogen, preferably fluorine or chlorine;

the term "$(C_1-C_6)$-alkylthio" is to be understood as meaning an alkylthio group whose hydrocarbon radical has the meaning given under the term "$(C_1-C_6)$-alkyl";

the term "$(C_1-C_6)$-haloalkylthio" is to be understood as meaning a $(C_1-C_6)$-alkylthio group in which one or more, in the case of fluorine optionally also all, hydrogen atoms of the hydrocarbon moiety are replaced by halogen, in particular chlorine or fluorine;

the term "$(C_1-C_6)$-alkylsulfinyl" is to be understood as meaning, for example, the methyl-, ethyl-, propyl-, isopropyl-, butyl-, isobutyl-, sec-butyl-, tert-butyl-, pentyl-, 2-methylbutyl- or hexylsulfinyl group;

the term "$(C_1-C_6)$-alkylsulfonyl" is to be understood as meaning, for example, the methyl-, ethyl-, propyl-, isopropyl-, butyl-, isobutyl-, sec-butyl-, tert-butyl-, pentyl-, 2-methylbutyl- or hexylsulfonyl group;

the terms "$(C_1-C_6)$-haloalkylsulfinyl" and "$(C_1-C_6)$-haloalkylsulfonyl" are to be understood as meaning ($C_1$–$C_6$)-alkylsulfinyl and -sulfonyl radicals having the meanings given above in which one or more, in the case of fluorine optionally also all, hydrogen atoms of the hydrocarbon moiety are replaced by halogen, in particular chlorine or fluorine;

the term "($C_1$–$C_6$)-alkoxy" is to be understood as meaning an alkoxy group whose hydrocarbon radical has the meaning given under the term "($C_1$–$C_6$)-alkyl";

the term "($C_1$–$C_6$)-alkylamino" is to be understood as meaning, for example, the methylamino, ethylamino, propylamino, isopropylamino, butylamino, isobutylamino, sec-butylamino, tert-butylamino, pentylamino or the hexylamino group;

the term "($C_1$–$C_6$)-dialkylamino" is to be understood as meaning, for example, the dimethylamino, methylethylamino, diethylamino, dipropylamino, dibutylamino, dipentylamino or the dihexylamino group; but also cyclic systems, such as, for example, the pyrrolidino or piperidino group, the term "($C_1$–$C_6$)-haloalkoxy" is to be understood as meaning a haloalkoxy group whose halohydrocarbon radical has the meaning given under the term "($C_1$–$C_6$)-haloalkyl";

the term "aryl" is to be understood as meaning a carbocyclic aromatic radical having preferably 6 to 14, in particular 6 to 12, carbon atoms, such as phenyl or naphthyl, preferably phenyl;

the term "heterocyclyl" is to be understood as meaning a heteroaromatic or heteroaliphatic ring system, where "heteroaromatic ring system" is to be understood as meaning an aryl radical in which at least one CH group is replaced by N and/or at least two adjacent CH groups are replaced by S, NH or O, for example a thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-triazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or 4H-quinolizine radical;

and the term "heteroaliphatic ring system" is to be understood as meaning a ($C_3$–$C_8$)-cycloalkyl radical in which at least one carbon unit is replaced by O, S or a group $NR^{11}$ and $R^{11}$ is hydrogen, ($C_1$–$C_4$)-alkyl, ($C_1$–$C_4$)-alkoxy or aryl;

the term "arylthio" is to be understood as meaning, for example, the phenylthio group;

the term "aryloxy" is to be understood as meaning, for example, the phenoxy group;

the term "heterocyclyloxy" or "heterocyclylthio" is to be understood as meaning one of the heterocyclic radicals mentioned above which is attached via an oxygen or sulfur atom;

the term "($C_3$–$C_8$)-cycloalkoxy" or "($C_3$–$C_8$)-cycloalkylthio" is to be understood as meaning one of the ($C_3$–$C_8$)-cycloalkyl radicals listed above which is attached via an oxygen or sulfur atom;

the term "($C_3$–$C_8$)-cycloalkoxycarbonyl" is to be understood as meaning, for example, the cyclobutyloxycarbonyl, cyclopentyloxycarbonyl, cyclohexyloxycarbonyl or the cycloheptyloxycarbonyl group;

and the term "unsubstituted or substituted aryl, heterocyclyl, phenyl, etc." is to be understood as meaning, preferably, substitution by one or more, preferably 1 to 3, in the case of halogen also up to the maximum number of, radicals selected from the group consisting of halogen, cyano, nitro, amino, hydroxyl, thio, ($C_1$–$C_4$)-alkyl, ($C_1$–$C_4$)-haloalkyl, ($C_3$–$C_8$)-cycloalkyl, ($C_1$–$C_4$)-haloalkylthio, ($C_1$–$C_4$)-alkylamino, ($C_1$–$C_4$)-haloalkylamino, formyl or ($C_1$–$C_4$)-alkanoyl.

The explanation given above applies correspondingly to homologs and radicals derived therefrom.

The present invention relates to the compounds of the formula (I) in the form of the free base or an acid addition salt. Acids which can be used for salt formation are, for example, inorganic acids, such as hydrochloric acid, hydrobromic acid, nitric acid, sulfuric acid, phosphoric acid, or organic acids, such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

In some cases, the compounds of the formula (I) contain one or more chiral carbon atoms or stereoisomers on double bonds. Enantiomers or diastereomers can therefore occur. The invention relates both to the pure isomers and to mixtures thereof. The mixtures of diastereomers can be separated into the components by customary methods, for example by selective crystallization from suitable solvents or by chromatography. Racemates can be separated into the enantiomers by customary methods, thus, for example, by salt formation with a chiral, enantiomerically pure acid, separation of the diastereomeric salts and liberation of the pure enantiomers by means of a base.

The compounds according to the invention are prepared by methods which are known per se from the literature, as described in standard works on organic synthesis, for example Houben-Weyl, Methoden der Organischen Chemie [Methods in Organic Chemistry], Georg-Thieme-Verlag, Stuttgart.

The preparation is carried out under reaction conditions which are known and suitable for the abovementioned reactions. Other variants which are known per se, but not illustrated here in greater detail, may also be used.

If desired, the starting materials may also be formed in situ, in such a way that they are not isolated from the reaction mixture but immediately reacted further to give the compounds of the formula (I).

The general chemistry of 1,3-oxazolines is described, for example, in Tetrahedron, 1994, 50, 2297–2360 and in Nachr. Chem. Tech. Lab. 1996, 44, 744–750.

The invention also provides a process for preparing compounds of the formula (I, G=3-isoxazinyl) by reacting 1,3-oxazolines, 1,3-thiazolines, pyrrolines and imidazolines of the formula (II) (see, for example, WO-A-96/22283) (suitably substituted by $X_n$ and $R^1_m$) with a halogenating agent to give compounds of the formula (III), and reacting these compounds with an olefin (IV) (suitably substituted by $R^5_l$), where initially an oxime of the formula (II), (II)

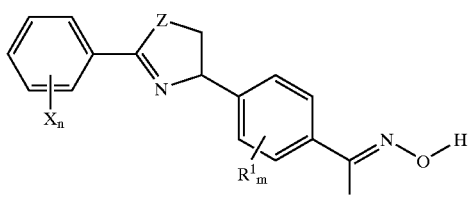

in which
X and Z have the meanings given in formula (I)
is reacted with a halogenating agent, preferably a chlorinating agent, to give a compound of the formula (III)

(III)

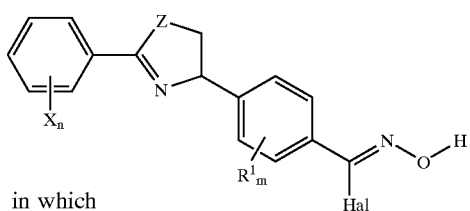

in which
Hal is halogen, preferably Cl,
and then reacted further with an olefin of the formula (IV), (IV)

in which $R^5$ and t have the meanings given above.

The invention also provides a process for preparing compounds of the formula (II) by reacting 1,3-oxazolines, 1,3-thiazolines, pyrrolines and imidazolines of the formula (V) (suitably substituted by X and $R^1$) with hydroxylamine or its salts, if appropriate in the presence of a base, (V)

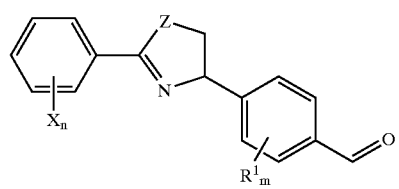

in which
$X_n$ and Z have the meanings given in formula (I).

The invention also provides a process for preparing compounds of the formula (V) from 1,3-oxazolines, 1,3-thiazolines, pyrrolines and imidazolines of the formula (VI) (suitably substituted by X and $R^1$), where compounds of the formula (VI)

(VI)

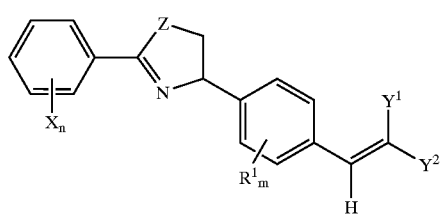

in which
$Y^1$ and $Y^2$ independently of one another are hydrogen, $(C_1-C_4)$-alkyl, $(C_1-C_4)$-alkoxycarbonyl or phenyl and $X_n$ and Z have the meanings given in formula (I) are reacted with an oxidizing agent to give compounds of the formula (V).

Methods A to D are illustrated using the synthesis of different subgroups of compounds of the formula (I), (G=3-isoxazinyl) as an example:

The isoxazole ring is advantageously generated in the presence of a base, for example selected from the group of the alkali metal hydroxides, alkali metal carbonates, alkoxides and amines.

Method A

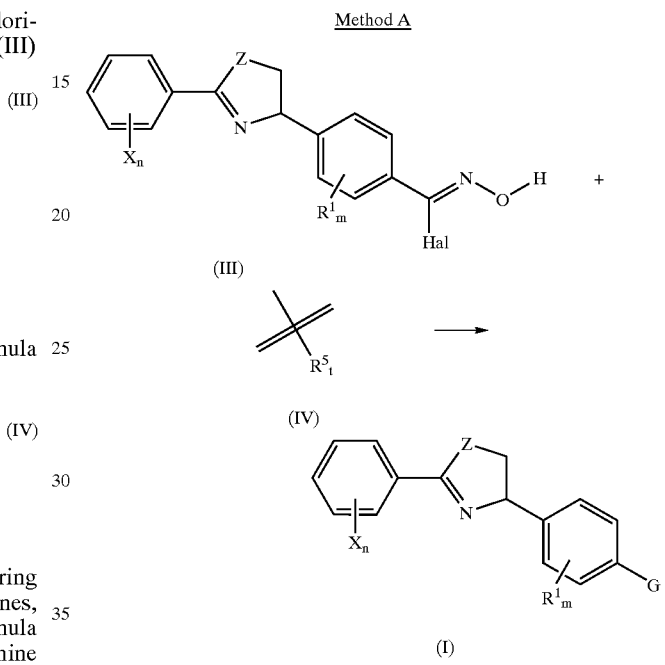

Using halogenating agents, oximes of the formula (II) are converted into the halooximes (III). Suitable halogenating agents are, for example, elemental halogen, hypohalites and N-haloimides:

Method B

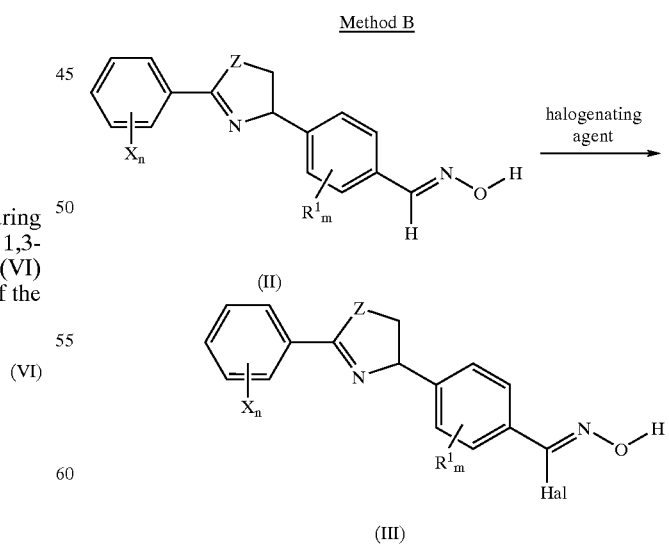

Oximes of the formula (II) are prepared by reacting aldehydes of the formula (V) with hydroxylamine or hydroxylamine salts, if appropriate in the presence of a base:

Method C

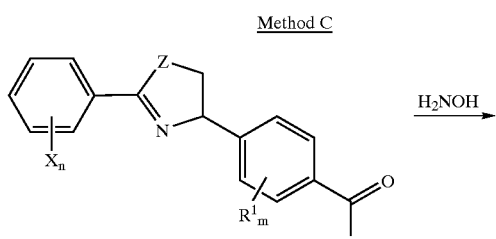

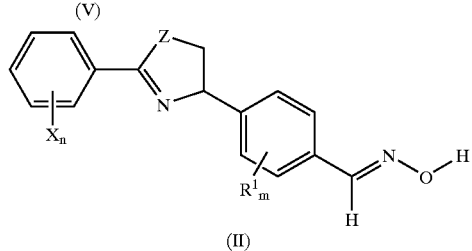

Aldehydes of the formula (V) are generated by cleaving the olefins of the formula (VI) using an oxidizing agent. Suitable oxidizing agents are, for example, ruthenium or osmium compounds in combination with a periodate, or ozone:

Method D

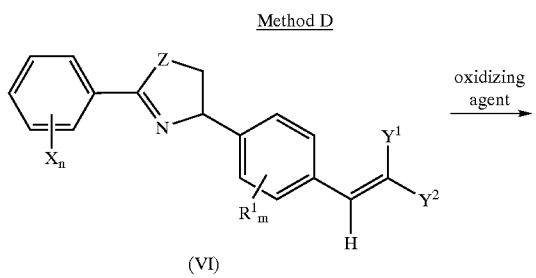

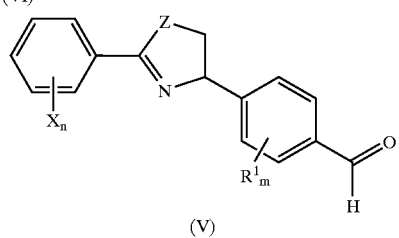

Some compounds of the formula (VI) have been described (WO-A-95/04726) or they can be prepared in a similar manner.

The invention also provides a process for preparing compounds of the formula (I) (G=5-isoxazinyl) by reacting 1,3-oxazolines, 1,3-thiazolines, pyrrolines and imidazolines of the formula (VII) (see, for example, WO-A 95/04726), suitably substituted by $X_n$ and $R^1_m$, with a halooxime, where an olefin of the formula (VII)

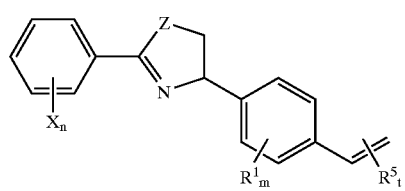

in which

Z and $R^5_t$ have the meanings given above, is reacted with a halooxime of the formula (VIII)

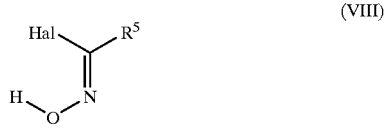

where $R^5$ has the meanings given above.

Method E is illustrated using the synthesis of compounds of the formula (I) (G=3-isoxazinyl) as an example:

The isoxazole ring is generated in the presence of a base, selected, for example, from the group consisting of alkali metal hydroxides, alkali metal carbonates, alkoxides and amines.

Method E

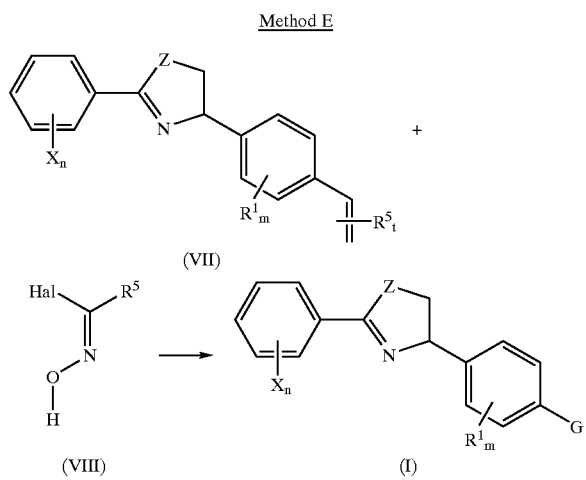

Various esters and amides as radicals $R^5$ can be prepared, for example, from acid derivatives. These, for their part, are obtainable, for example, by ester hydrolysis, for example

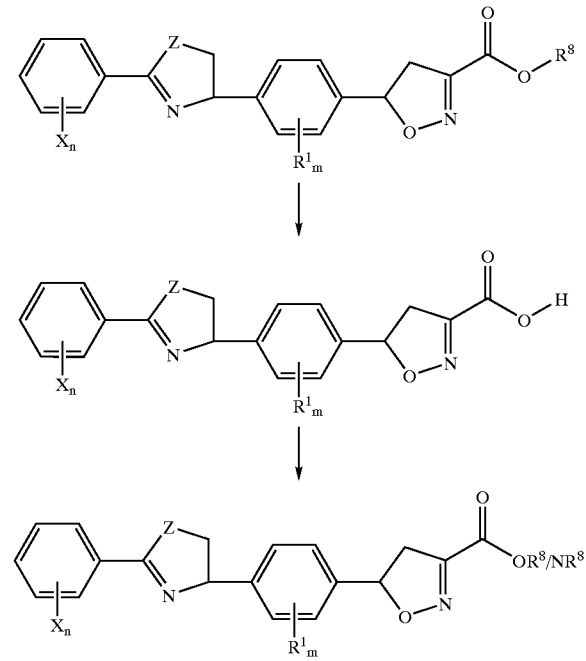

Suitable for use as hydrolyzing agents are, for example, aqueous alkali metal hydroxide solutions.

During the preparation of the amides or esters, the acid can be activated using, for example, a carbodiimide, carbonyldiimidazole or an inorganic acid chloride, for example thionyl chloride.

Various esters and amides as radical $R^5$ can also be prepared, for example, from hydroxyl and amine derivatives. These, for their part, are obtainable, for example, by ester or amide hydrolysis, for example:

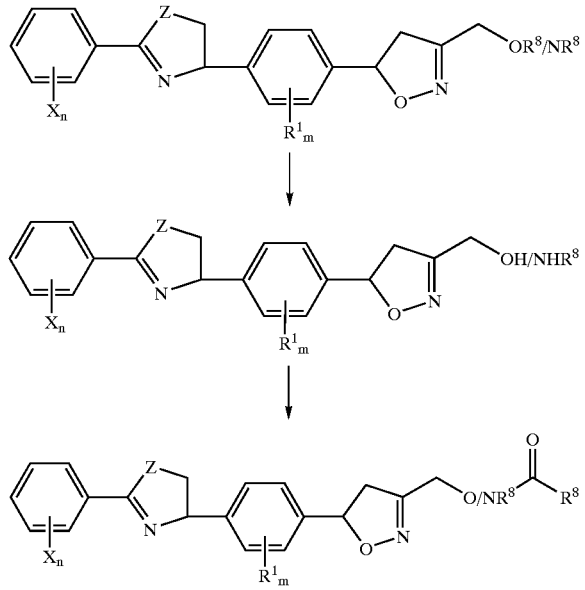

Suitable for use as hydrolyzing agents are, for example, aqueous alkali metal hydroxide solutions.

To prepare the amides or esters, the alcohol or the amine can be reacted, for example, with an activated acid, e.g. an acid chloride.

Collections of compounds of the formula (I) which can be synthesized by the abovementioned scheme may also be prepared in a parallel manner and this may be effected manually or in a semiautomated or fully automated manner. In this case, it is possible, for example, to automate the procedure of the reaction, the work-up or the purification of the products or of the intermediates. In total, this is to be understood as meaning a procedure as is described, for example, by S. H. DeWitt in "Annual Reports in Combinatorial Chemistry and Molecular Diversity: Automated synthesis", Volume 1, Verlag Escom 1997, pages 69 to 77.

A number of commercially available apparatuses as are offered by, for example, Stem Corporation, Woodrolfe Road, Tollesbury, Essex, CM9 8SE, England or H+P Labortechnik GmbH, Bruckmannring 28, 85764 Oberschleißheim, Germany, may be used for the parallel procedure of the reaction and work-up. For the parallel purification of compounds of the formula (I), or of intermediates obtained during the preparation, use may be made, inter alia, of chromatography apparatuses, for example those from ISCO, Inc., 4700 Superior Street, Lincoln, NE 68504, USA.

The apparatuses mentioned lead to a modular procedure in which the individual process steps are automated, but manual operations have to be performed between the process steps. This can be avoided by employing semiintegrated or fully integrated automation systems where the automation modules in question are operated by, for example, robots. Such automation systems can be obtained, for example, from Zymark Corporation, Zymark Center, Hopkinton, MA 01748, USA.

In addition to what has been described here, compounds of the formula (I) may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example Barry A. Bunin in "The Combinatorial Index", Verlag Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131–5135), in which products from IRORI, 11149 North Torrey Pines Road, La Jolla, Calif. 92037, USA, are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The preparation according to the processes described herein yields compounds of the formula (I) in the form of substance collections which are referred to as libraries. The present invention also relates to libraries which comprise at least two compounds of the formula (I).

The compounds of the formula (I) are suitable for controlling animal pests, in particular insects, arachnids, helminths and molluscs, very especially preferably for controlling insects and arachnids, which are encountered in agriculture, in livestock breeding, in forests, in the protection of stored goods and materials and in the hygiene sector, and have good plant tolerance and favorable toxicity to warm-blooded species. They are active against normally sensitive and resistant species and against all or individual development stages. The abovementioned pests include:

From the order of the Acarina, for example, Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp., Eotetranychus spp., Oligonychus spp. and Eutetranychus spp.

From the order of the Isopoda, for example, Oniscus asselus, Armadium vulgare and Porcellio scaber.

From the order of the Diplopoda, for example, Blaniulus guttulatus.

From the order of the Chilopoda, for example, Geophilus carpophagus and Scutigera spp.

From the order of the Symphyla, for example, Scutigerella immaculata.

From the order of the Thysanura, for example, Lepisma saccharina.

From the order of the Collembola, for example, Onychiurus armatus.

From the order of the Orthoptera, for example, Blatta orientalis, Periplaneta americana, Leucophaea madeira, Blattella germanica, Acheta domesticus, Gryllotalpa spp., Locusta migratoria migratorioides, Melanoplus differentialis and Schistocerca gregaria.

From the order of the Isoptera, for example, Reticulitermes spp.

From the order of the Anoplura, for example, Phylloera vastatrix, Pemphigus spp., Pediculus humanus corporis, Haematopinus spp. and Linognathus spp.

From the order of the Mallophaga, for example, Trichodectes spp. and Damalinea spp.

From the order of the Thysanoptera, for example, Hercinothrips femoralis and Thrips tabaci.

From the order of the Heteroptera, for example, Eurygaster spp., Dysdercus intermedius, Piesma quadrata, Cimex lectularius, Rhodnius prolixus and Triatoma Spp.

From the order of the Homoptera, for example, Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelus bilobatus, Nephotettix cincticeps, Lecanium comi, Saissetia oleae, Laodelphax striatellus, Nilaparvata lugens, Aonidiella aurantii, Aspidiotus hederae, Pseudococcus spp. and Psylla spp.

From the order of the Lepidoptera, for example, Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima and Tortrix viridana.

From the order of the Coleoptera, for example, Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylloides chrysocephala, Epilachna varivestis, Atomaria spp., Oryzaephilus surinamensis, Anthonumus spp., Sitophilus spp., Otiorrhynchus sulcatus, Cosmopolites sordidus, Ceuthorrynchus assimilis, Hypera postica, Dermestes spp., Trogoderma, Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis and Costelytra zealandica.

From the order of the Hymenoptera, for example, Diprion spp., Hoplocampa spp., Lasius spp., Monomorium pharaonis and Vespa spp.

From the order of the Diptera, for example, Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hypobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa.

From the order of the Siphonaptera, for example, Xenopsylla cheopsis and Ceratophyllus spp.

From the order of the Arachnida, for example, Scorpio maurus and Latrodectus mactans.

From the class of helminths, for example, Haemonchus, Trichostrongulus, Ostertagia, Cooperia, Chabertia, Strongyloides, Oesophagostomum, Hyostrongulus, Ancylostoma, Ascaris and Heterakis, as well as Fasciola.

From the class of the Gastropoda, for example, Deroceras spp., Arion spp., Lymnaea spp., Galba spp., Succinea spp., Biomphalaria spp., Bulinus spp. and Oncomelania spp.

From the class of Bivalva, for example, Dreissena spp.

The phytoparasitic nematodes which can be controlled according to the invention include, for example, the root-parasitic soil nematodes, such as, for example, those of the genera Meloidogyne (root gall nematodes, such as Meloidogyne incognita, Meloidogyne hapla and Meloidogyne javanica), Heterodera and Globodera (cyst-forming nematodes, such as Globodera rostochiensis, Globodera pallida and Heterodera trifolii) and of the genera Radopholus, such as Radopholus similis, Pratylenchus, such as Pratylenchus neglectus, Pratylenchus penetrans and Pratylenchus curvitatus, Tylenchulus, such as Tylenchulus semipenetrans, Tylenchorhynchus, such as Tylenchorhynchus dubius and Tylenchorhynchus claytoni, Rotylenchus, such as Rotylencus robustus, Heliocotylenchus, such as Heliocotylenchus multicinctus, Belonoaimus, such as Belonoaimus longicaudatus, Longidorus, such as Longidorus elongatus, Trichodorus, such as Trichodorus primitivus and Xiphinema, such as Xiphinema index.

The nematode genera Ditylenchus (stem parasites, such as Ditylenchus dipsaci and Ditylenchus destructor), Aphelenchoides (leaf nematodes, such as Aphelenchoides ritzemabosi) and Anguina (blossom nematodes, such as Anguina tritici) can furthermore be controlled with the compounds according to the invention.

The invention also relates to compositions, for example crop protection compositions, preferably insecticidal, acaricidal, ixodicidal, nematicidal, molluscidal or fungicidal, particularly preferably insecticidal and acaricidal compositions, which comprise one or more compounds of the formula (I) in addition to suitable formulation auxiliaries.

In general, the compositions according to the invention comprise from 1 to 95% by weight of the active compounds of the formula (I).

For preparing the compositions according to the invention, the active compound and the other additives are combined and formulated as a suitable use form.

They can be formulated in various ways, depending on how this is predetermined by the biological and/or chemico-physical parameters. Suitable formulation possibilities are therefore:

Wettable powders (WP), emulsifiable concentrates (EC), aqueous solutions (SL), emulsions, sprayable solutions, oil- or water-based dispersions (SC), suspoemulsions (SE), dusting powders (DP), seed dressings, granules in the form of microgranules, sprayed granules, absorption granules and adsorption granules, water-dispersible granules (WG), ULV formulations, microcapsules, waxes or baits.

These individual types of formulation are known in principle and are described, for example, in: Winnacker-Küchler, "Chemische Technologie" [Chemical Technology], Volume 7, C. Hanser Verlag Munich, 4th Edition 1986; van Falkenberg, "Pesticides Formulations", Marcel Dekker N.Y., 2nd Edition 1972–73; K. Martens, "Spray Drying Handbook", 3rd Edition 1979, G. Goodwin Ltd. London.

The necessary formulation auxiliaries, such as inert materials, surfactants, solvents and further additives, are likewise known and are described, for example, in: Watkins, "Handbook of Insecticide Dust Diluents and Carriers", 2nd Edition, Darland Books, Caldwell N. J.; H. v. Olphen, "Introduction to Clay Colloid Chemistry", 2nd Edition, J. Wiley & Sons, N.Y.; Marsden, "Solvents Guide", 2nd Edition, Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1967; Winnacker-Küchler, "Chemische Technologie" [Chemical Technology], Volume 7, C. Hanser Verlag Munich, 4th Edition 1986.

Combinations with other substances having a pesticidal action, fertilizers and/or growth regulators can be prepared on the basis of these formulations, for example in the form of a ready-to-use formulation or as a tank mix. Wettable powders are preparations which are uniformly dispersible in water and which, alongside the active compound, and in addition to a diluent or inert substance, also comprise wetting agents, for example polyethoxylated alkylphenols, polyethoxylated fatty alcohols or alkyl- or alkylphenolsulfonates, and dispersing agents, for example sodium ligninsulfonate or sodium 2,2'-dinaphthylmethane-6,6'-disulfonate.

Emulsifiable concentrates are prepared by dissolving the active compound in an organic solvent, for example butanol, cyclohexanone, dimethylformamide, xylene or also higher-boiling aromatics or hydrocarbons, with the addition of one or more emulsifiers. Emulsifiers which can be used are, for example: calcium alkylaryl-sulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting powders are obtained by grinding the active compound with finely divided solid substances, for example talc, naturally occurring clays, such as kaolin, bentonite and pyrophyllite, or diatomaceous earth. Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

In wettable powders, the active compound concentration is for example about 10 to 90% by weight, the remainder to make up 100% by weight comprising customary formulation constituents. In emulsifiable concentrates, the active compound concentration can be about 5 to 80% by weight. Dust-like formulations usually comprise 5 to 20% by weight of active compound, and sprayable solutions about 2 to 20% by weight. In granules, the content of active compound partly depends on whether the active compound is present in liquid or solid form and what granulating auxiliaries, fillers and the like are used.

In addition, the active compound formulations mentioned comprise, if appropriate, the particular customary tackifiers, wetting agents, dispersing agents, emulsifiers, penetration agents, solvents, fillers or carrier substances.

For use, the concentrates in the commercially available form are diluted in the customary manner, if appropriate, for example by means of water in the case of wettable powders, emulsifiable concentrates, dispersions and in some cases also microgranules. Dust-like and granular formulations as well as sprayable solutions are usually not diluted further with additional inert substances before use.

The required amount applied varies with the external conditions, such as temperature or humidity. It can vary within wide limits, for example between 0.0005 and 10.0 kg/ha or more of active substance, but is preferably between 0.001 and 5 kg/ha.

The active compounds according to the invention can be present in their commercially available formulations and in the use forms prepared from these formulations (see the above mentioned compositions) as mixtures with other active compounds, such as insecticides, attractants, sterilizing agents, acaricides, nematicides, fungicides, molluscides, growth-regulating substances or herbicides.

The pesticides include, for example, phosphoric acid esters, carbamates, carboxylic acid esters, formamidines, tin compounds and substances produced by microorganisms.
Preferred Partners for the Mixtures are:
1. from the group of phosphorus compounds acephate, azamethiphos, azinphos-ethyl, azinphos-methyl, bromophos, bromophosethyl, cadusafos (F-67825), chlorethoxyphos, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, dimethoate, disulfoton, EPN, ethion, ethoprophos, etrimfos, famphur, fenamiphos, fenitriothion, fensulfothion, fenthion, fonofos, formothion, fosthiazate (ASC-66824), heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosphocarb (BAS-301), phosmet, phosphamidon, phoxim, pirimiphos, primiphosethyl, pirimiphos-methyl, profenofos, propaphos, proetamphos, prothiofos, pyraclofos, pyridapenthion, quinalphos, sulprofos, temephos, terbufos, tebupirimfos, tetrachlorvinphos, thiometon, triazophos, trichlorphon, vamidothion;
2. from the group of carbamates alanycarb (OK-135), aldicarb, 2-sec-butylphenyl methylcarbamate (BPMC), carbaryl, carbofuran, carbosulfan, cloethocarb, benfuracarb, ethiofencarb, furathiocarb, HCN-801, isoprocarb, methomyl, 5-methyl-m-cumenyl butyryl (methyl)carbamate, oxamyl, pirimicarb, propoxur, thiodicarb, thiofanox, 1-methylthio(ethylideneamino) N-methyl-N-(morpholinothio)carbamate (UC 51717), triazamate;
3. from the group of carboxylic acid esters acrinathrin, allethrin, alphametrin, 5-benzyl-3-furylmethyl (E)-(1R)-cis-2,2-di-methyl-3-(2-oxothiolan-3-ylidenemethyl) cyclopropanecarboxylate, beta-cyfluthrin, beta-cypermethrin, bioailethrin, bioallethrin ((S)-cyclopentyl isomer), bioresmethrin, bifenthrin, (RS)-1-cyano-1-(6-phenoxy-2-pyridyl)methyl (1RS )-trans-3-(4-tert-butylphenyl)-2,2-dimethylcyclopropanecarboxylate (NCI 85193), cycloprothrin, cyfluthrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), imiprothrin (S-41311), lambda-cyhalothrin, permethrin, pheothrin ((R) isomer), prallethrin, pyrethrins (natural products), resmethrin, tefluthrin, tetramethrin, theta-cypermethrin (TD-2344), tralomethrin, transfluthrin and zeta-cypermethrin (F-56701);
4. from the group of amidines amitraz, chlordimeform;
5. from the group of tin compounds cyhexatin, fenbutatin oxide;
6. others abamectin, ABG-9008, acetamiprid, Anagrapha falcitera, AKD-1022, AKD-3059, ANS-118, Bacillus thuringiensis, Beauveria bassianea, bensultap, bifenazate (D-2341), binapacryl, BJL-932, bromopropylate, BTG-504, BTG-505, buprofezin, camphechlor, cartap, chlorobenzilate, chlorfenapyr, chlorfluazuron, 2-(4-chlorophenyl)-4,5-diphenylthiophene (UBI-T 930), chlorfentezine, chromafenozide (ANS-118), CG-216, CG-217, CG-234, A-184699, 2-naphthylmethyl cyclopropanecarboxylate (Ro12-0470), cyromazin, diacloden (thiamethoxam), diafenthiuron, N-(3,5-dichloro-4-(1,1,2,3,3,3-hexafluoro-1-propyloxy)phenyl)carbamoyl)-2-chlorobenzocarboxamide acid ethyl ester, DDT, dicofol, diflu benzuron, N-(2,3-dihydro-3-methyl-1,3-thiazol-2-ylidene)-2,4-xylidine, dinobuton, dinocap, diofenolan, DPX-062, emamectin-benzoate (MK-244), endosulfan, ethiprole (sulfethiprole), ethofenprox, etoxazole (YI-5301), fenazaquin, fenoxycarb, fipronil, fluazuron, flumite (flufenzine, SZI-121), 2-fluoro-5-(4-(4-ethoxyphenyl)-4-methyl-1-pentyl)diphenyl ether (MTI 800), granulosis and nuclear polyhedrosis viruses, fenpyroximate, fenthiocarb, flubenzimine, flucycloxuron, flufenoxuron, flufenprox (ICI-A5683), fluproxyfen, gamma-HCH, halofenozide (RH-0345), halofenprox (MTI-732), hexaflumuron (DE_473), hexythiazox, HOI-9004, hydramethyinon (AC 217300), IKI 220, imidacloprid, indoxacarb (DPX-MP062), kanemite (AKD-2023), M-020, MTI446, ivermectin, lufenuron, M-020, methoxyfenozide (Intrepid, RH-2485), milbemectin, NC-196, neemgard, nitenpyram (TI-304), 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), pyriproxyfen (S-71639), NC-196, NC-1111, NNI-9768, novaluron (MCW-275), OK-9701, OK-9601, OK-9602, propargite, pymethrozine, pyridaben, pyrimidifen (SU-8801), RH-0345, RH-2485, RYI-210, S-1283, S-1833, SB7242, SI-8601, silafluofen, silomadine (CG-177), spinosad, SU-9118, tebufenozide, tebufenpyrad (MK-239), teflubenzuron, tetradifon, tetrasul, thiacloprid, thiocyclam, TI435, tolfenpyrad (OMI-88), triazamate (RH-7988), triflumuron, verbutin, vertalec (Mykotal), YI-5301.

The active compound content of the use forms prepared from the commercially available formulations can be from 0.00000001 to 95% by weight of active compound, preferably between 0.00001 and 1% by weight. The active compounds are used in a customary manner appropriate for the use forms.

The invention also provides a method for controlling harmful insects, Acarina, molluscs and/or nematodes, in which an effective amount of a compound according to the invention or a composition according to the invention is applied to these organisms or the plants, areas or substrates infested with them.

The invention also provides the use of a compound according to the invention or a composition according to the invention for controlling harmful insects, Acarina, molluscs and/or nematodes.

The active substances according to the invention are also suitable for the field of veterinary medicine, preferably for controlling endo- and ectoparasites, and for the field of animal husbandry.

The active substances according to the invention can preferably be applied in a known manner, such as by oral application in the form of, for example, tablets, capsules, potions or granules, by dermal application in the form of, for example, dipping, spraying, pouring-on and spotting-on and dusting, and also by parenteral application in the form of, for example, injection.

The compounds of the formula (I) according to the invention can accordingly also be employed particularly advantageously in livestock husbandry (for example cattle, sheep, pigs and poultry such as chickens, geese etc.). In a preferred embodiment of the invention, the novel compounds, if appropriate in suitable formulations (cf. above) and if appropriate with the drinking water or feed, are administered orally to the animals. Since excretion in the feces occurs in an effective fashion, the development of insects in the animal feces can be prevented very simply in this fashion. The dosages and formulations suitable in each case, in particular, depend on the type and developmental stage of the productive animals and also on the severity of infestation and can easily be determined and fixed by conventional methods. In the case of cattle, the compounds can be employed, for example, in dosages of 0.01 to 1 mg/kg of body weight.

Accordingly, the invention also provides the use of a compound of the formula (I) or one of the abovementioned compositions for preparing a veterinary medicament.

In addition, the compounds according to the invention are also suitable for use in industrial fields, for example as wood preservative, as preservative in paints, in cooling lubricants for metal working or as preservative in drilling and cutting oils.

Compounds of the formula (I) in their commercially available formulations can be used either alone or in combination with other fungicides known from the literature.

Examples of fungicides which are known from the literature and which can be combined in accordance with the invention with the compounds of the formula (I) are the following products:

aldimorph, andoprim, anilazine, BAS 480F, BAS 450F, benalaxyl, benodanil, benomyl, binapacryl, bitertanol, bromuconazole, buthiobate, captafol, captan, carbendazim, carboxin, CGA 173506, cyprofuram, dichlofluanid, dichlomezin, diclobutrazol, diethofencarb, difenconazole (CGA 169374), difluconazole, dimethirimol, dimethomorph, diniconazole, dinocap, dithianon, dodemorph, dodine, edifenfos, ethirimol, etridiazol, fenarimol, fenfuram, fenpiclonil, fenpropidin, fenpropimorph, fentin acetate, fentin hydroxide, ferimzone (TF164), fluazinam, fluobenzimine, fluquinconazole, fluorimide, flusilazole, flutolanil, flutriafol, folpet, fosetyl-aluminum, fuberidazole, fulsulfamide (MT-F 651), furalaxyl, furconazole, furmecyclox, guazatine, hexaconazole, ICI A5504, imazalil, imibenconazole, iprobenfos, iprodione, isoprothiolane, KNF 317, copper compounds such as copper oxychloride, oxine-copper, copper oxide, mancozeb, maneb, mepanipyrim (KIF 3535), metconaole, mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyroquilon, rabenzazole, RH7592, sulfur, tebuconazole, TF 167, thiabendazole, thicyofen, thiofanate-methyl, thiram, tolclofos-methyl, tolylfluanid, triadimefon, triadimenol, tricyclazole, tridemorph, triflumizole, triforine, validamycin, vinchlozolin, XRD 563, zineb, sodium dodecylsulfonate, sodium dodecyl sulfate, sodium C13/C15-alcohol ether sulfonate, sodium cetostearyl phosphate ester, sodium dioctylsulfosuccinate, sodium isopropylnaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quaternized fatty amines, alkyldimethylbenzylammonium chloride and 1-hydroxylethyl-2-alkylimidazoline.

The abovementioned components are known active substances, many of which are described in C. D. S. Tomlin, S. B. Walker, The Pesticide Manual, 12th Edition, British Crop Protection Council, Farnham 2000.

The invention also provides seed, comprising or coated with an effective amount of a compound according to the invention or of a composition according to the invention.

The compounds of the formula (I) can also be employed for controlling harmful organisms in crops of known or genetically engineered plants yet to be developed. As a rule, the transgenic plants are distinguished by particular advantageous properties, for example by resistances to certain crop protection agents, resistances to plant diseases or pathogens of plant diseases such as certain insects or microorganisms such as fungi, bacteria or viruses. Other particular properties relate, for example, to the harvested material with regard to quantity, quality, storage properties, composition and specific constituents. Thus, transgenic plants with an elevated starch content or altered starch quality, or those with a different fatty acid spectrum of the harvested material, are known.

The use in economically important transgenic crops of useful plants and ornamentals, for example, cereals such as wheat, barley, rye, oats, millet and sorghum, rice, cassava and maize or else crops of sugar beet, cotton, soya, oilseed rape, potatoes, tomatoes, peas and other vegetables is preferred.

When being use in transgenic crops, in particular those in which the plants express an insecticide, effects are frequently found (in addition to the pesticidal effects which can be observed in other crops) which are specific to application in the transgenic crop in question, for example an altered or specifically widened spectrum of pests which can be controlled, or altered application rates which can be used for application.

The invention therefore also provides the use of compounds of the formula (I) for controlling harmful organisms in transgenic crop plants.

The use according to the invention of compounds of the formula (I) or compositions comprising them, for example an insecticide, acaricide, molluscide or nematicide, includes the case where the compound of the formula (I) or its salt is formed from a precursory substance only after application, for example in the insect, in a plant or in the soil.

The contents of german patent application 101 14 597.7, whose priority is claimed by the present application, and the contents of the appended summary are hereby incorporated herein by reference; they are.

The examples which follow serve to illustrate the invention without restricting it thereto.

A. PREPARATION EXAMPLES

3-Arylisoxazolines

Intermediate I2: 2-(2,6-difluorophenyl)-4-(4-(2-phenylethenyl)phenyl)oxazoline 2-(2,6-Difluorophenyl)-4-(4-bromophenyl)oxazoline (33.8 g, 0.1 mol) and styrene (22.9 ml, 0.2 mol) in 300 ml of DMF were heated at reflux with sodium carbonate (11.66 g, 0.11 mol), tris(2,4-di-tert-butylphenyl)phosphite (6.47 g, 10 mmol) and palladium acetate (0.45 g, 2 mmol) for 20 h. Following extractive work-up with ethyl acetate, the residue was triturated with heptane/dichloromethane (1:1). This gave 27 g of crystals, m.p. 141° C.

Intermediate I2: 2-(2,6-Difluorophenyl)-4-(4-formylphenyl)oxazoline

At 0° C., 2-(2,6-difluorophenyl-)4-(4-(2-phenylethenyl)phenyl)oxazoline (7.22 g, 20 mmol) and sodium metaperiodate (8.55 g, 20 mmol) were suspended in acetonitrile/acetone/water (1:1:1, 180 ml), and a catalytic amount of ruthenium trichloride hydrate was added. Following extractive work-up with ethyl acetate and column chromatography, 5.6 g of the aldehyde were obtained as a viscous oil.

Intermediate I3: 2-(2,6-difluorophenyl)-4-(4-(hydroxyiminomethyl)phenyl)oxazoline At room temperature, 2-(2,6-difluorophenyl)-4-(4-formylphenyl)oxazoline (5.6 g), hydroxylamine hydrochloride (1.53 g, 1.1 equivalents) and sodium acetate (4.9 g, 3 equivalents) were stirred in 50 ml of ethanol for 24 h. Following extractive work-up with ethyl acetate and column chromatography, 4.2 g of crystals were obtained, m.p. 159° C.

2-(2,6-Difluorophenyl)-4-(4-(5-tert-butylisoxazolin-3-yl)phenyl)oxazoline (Ex No. 9)

At 50° C., 2-(2,6-difluorophenyl)-4-(4-(hydroxyiminomethyl)phenyl)oxazoline (40 mg, 0.13 mmol) and N-chlorosuccinimide (19 mg, 1.1 equivalents) in 2 ml of DMF were heated for 4 h. After cooling to room temperature, 3,3-dimethylbutene (33 mg, 0.4 mmol) and triethylamine (41 mg, 0.4 mmol) were added. After 16 h of stirring, the mixture was worked up by extraction with ethyl acetate and the residue was purified by column chromatography. This gave 19 mg of product.

2-(2,6-Difluorophenyl)-4-(4-(5-trifluoromethylisoxazolin-3-yl)phenyl )oxazoline (Ex. No. 43)

At 50° C., 2-(2,6-difluorophenyl)-4-(4-(hydroxyiminomethyl)phenyl)oxazoline (40 mg, 0.13 mmol) and N-chlorosuccinimide (19 mg, 1.1 equivalents) in 2 ml of DMF were heated for 4 h. After cooling to room temperature, 2 ml of a DMF solution saturated with 3,3,3-trifluoropropene, and triethylamine (41 mg, 0.4 mmol) were added. After 16 h of stirring, the mixture was worked up by extraction with ethyl acetate and the residue was purified by column chromatography. This gave 37 mg of product.

2-(2,6-Difluorophenyl)-4-(4-(5-(trifluoroacetamidomethyl) isoxazolin-3-yl)phenyl)oxazoline (Ex. No.115)

At 50° C., 2-(2,6-difluorophenyl)-4-(4-(hydroxyiminomethyl)phenyl)oxazoline (1.2 g, 4 mmol) and N-chlorosuccinimide (560 mg, 1.05 equivalents) in 6 ml of DMF were heated for 4 h. After cooling to room temperature, N-allyltrifluoroacetamide (2.75 g, 3 equivalents) and triethylamine (1.66 ml, 3 equivalents) were added. After 16 h of stirring, the mixture was worked up by extraction with ethyl acetate and the residue was purified by column chromatography. This gave 920 mg of product.

2-(2,6-Difluorophenyl)-4-(4-(5-(propionylaminomethyl) isoxazolin-3-yl)phenyl)-oxazoline (Ex. No. 116)

2-(2,6-Difluorophenyl)-4-(4-(5-(trifluoroacetamidomethyl)isoxazolin-3-yl)phenyl)-oxazoline (43 mg) in 2 ml of methanol was admixed with 0.5 ml of 2N aqueous sodium hydroxide solution, and the mixture was stirred for 16 h. Following extractive work-up with dichloromethane, triethylamine (0.05 ml) and propionyl chloride (50 mg) were added at 0° C. to the crude amine in 2 ml of dichlromethane. After 2 h of stirring, the mixture was worked up by extraction with ethyl acetate and the residue was purified by column chromatography. This gave 40 mg of product.

5-Arylisoxazolines

Intermediate I4: 2-(2,6-difluorophenyl)-4-(4-ethenylphenyl) oxazoline

In an autoclave, 2-(2,6-difluorophenyl)-4-(4-bromophenyl)oxazoline (6.0 g, 18 mmol), sodium carbonate (2.9 g, 21 mmol), tris(2,4-di-tert-butylphenyl) phosphite (1.2 g, 1.8 mmol) and palladium acetate (64 mg, 2% equivalents) in 100 ml of DMF were heated under 20 bar of ethylene at 150° C. for 44 h. Extractive work-up with ethyl acetate and column chromatography gave 3.75 g of crystals, m.p. 76° C.

2-(2,6-Difluorophenyl)-4-(4-(3-methylisoxazolin-5-yl) phenyl)oxazoline (Ex. No. 566)

At room temperature, acetaldoxime (30 mg, 0.5 mmol) and N-chlorosuccinimide (67 mg, 1 equivalent) in 3 ml of DMF were stirred for 3 h. 2-(2,6-Difluorophenyl)-4-(4-ethenylphenyl)oxazoline (43 mg, 0.15 mmol) and triethylamine (46 mg, 0.45 mmol) were then added, and the mixture was stirred for 16 h. Extractive work-up with ethyl acetate and column chromatography gave 32 mg of product.

2-(2,6-Difluorophenyl)-4-(4-(3-tert-butylisoxazolin-5-yl) phenyl)oxazoline (Ex. No. 573)

At room temperature, pivalaldehyde oxime (51 mg, 0.5 mmol) and N-chloro-succinimide (67 mg, 1 equivalent) in 3 ml of DMF were stirred for 3 h. 2-(2,6-Difluorophenyl)-4-(4-ethenylphenyl)oxazoline (43 mg, 0.15 mmol) and triethylamine (46 mg, 0.45 mmol) were then added, and the mixture was stirred for 16 h. Extractive work-up with ethyl acetate and column chromatography gave 30 mg of product.

2-(2,6-Difluorophenyl)-4-(4-(3-ethoxycarbonylisoxazolin-5-yl)phenyl)oxazoline (Ex. No. 614)

At 0° C., triethylamine (0.33 ml, 1.05 equivalents) was added to 2-(2,6-difluoro-phenyl)-4-(4-ethenylphenyl) oxazoline (570 mg, 2 mmol) and ethyl 2-chloro-2-hydroxyimino acetate (320 mg, 1.05 equivalents) in 10 ml of dichloroethane, and the mixture was stirred at room temperature for 16 h. Extractive work-up with ethyl acetate and column chromatography gave 420 mg of product.

2-(2,6-Difluorophenyl)-4-(4-(3-(2,2,2-trifluoroethylaminocarbonyl)isoxazolin-5-yl)phenyl)oxazoline (Ex. No. 628)

2-(2,6-Difluorophenyl)-4-(4-(3-ethoxycarbonylisoxazolin-5-yl)phenyl)oxazoline (769 mg, 1.9 mmol) in 20 ml of ethanol and 6.5 ml of 2N aqueous sodium hydroxide solution was stirred at room temperature for 3 h. The mixture was acidified with 2N hydrochloric acid and then worked up by extraction with dichloromethane. This gave 715 mg of crude acid which could be directly employed further.

47 mg (0.13 mmol) of the crude acid in 2 ml of DMF were admixed with hydroxybenzotriazole (18 mg, 1 equivalent) and N-ethyl-N'-(3-dimethylamino-propyl)carbodiimide (25 mg, 1 equivalent). Ethyldiisopropylamine (17 mg, 1 equivalent) in 1 ml of THF and 2,2,2-trifluoroethylamine (0.015 ml) in 1 ml of THF were then added. The mixture was stirred at 50° C. for 16 h, and then worked up by extraction with ethyl acetate and column chromatography, giving 41 mg of product.

B. CHEMICAL EXAMPLES (Tables 1–4)

TABLE 1

Oxazolines of the formula (I), Z = O, G = 3-isoxazolinyl

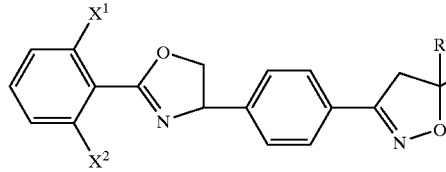

| Ex. No. | $X^1$ | $X^2$ | R' | R" | Physical data |
|---|---|---|---|---|---|
| 1 | F | F | H | H | NMR |
| 2 | F | F | H | $CH_3$ | NMR |
| 3 | " | " | " | $C_2H_5$ | |
| 4 | " | " | " | $n\text{-}C_3H_7$ | |
| 5 | " | " | " | $i\text{-}C_3H_7$ | NMR |
| 6 | " | " | " | $n\text{-}C_4H_9$ | |
| 7 | " | " | " | $i\text{-}C_4H_9$ | |
| 8 | " | " | " | $s\text{-}C_4H_9$ | |
| 9 | " | " | " | $t\text{-}C_4H_9$ | NMR |
| 10 | " | " | " | $n\text{-}C_6H_{13}$ | NMR |
| 11 | " | " | " | $CH_2\text{-}t\text{-}Bu$ | NMR |
| 12 | " | " | " | $CH_2Cl$ | NMR |
| 13 | " | " | " | $CH_2Br$ | NMR |
| 14 | F | F | $CH_3$ | $CH_3$ | |
| 15 | " | " | " | $C_2H_5$ | |
| 16 | " | " | " | $n\text{-}C_3H_7$ | |
| 17 | " | " | " | $i\text{-}C_3H_7$ | |
| 18 | " | " | " | $s\text{-}C_4H_9$ | NMR |
| 19 | " | " | " | $i\text{-}C_4H_9$ | NMR |
| 20 | " | " | " | $t\text{-}C_4H_9$ | NMR |
| 21 | " | " | " | $n\text{-}C_6H_{13}$ | |
| 22 | " | " | " | $CH_2\text{-}t\text{-}Bu$ | NMR |
| 23 | " | " | " | $CH_2Cl$ | NMR |
| 24 | F | F | H | $OCH_3$ | |
| 25 | " | " | " | $OC_2H_5$ | |
| 26 | " | " | " | $O\text{-}n\text{-}C_3H_7$ | |
| 27 | " | " | " | $O\text{-}n\text{-}C_4H_9$ | |
| 28 | " | " | " | $O\text{-}i\text{-}C_4H_9$ | NMR |
| 29 | " | " | " | CN | NMR |
| 30 | " | " | " | $CH_2CN$ | |
| 31 | " | " | " | $CH_2OCH_3$ | |
| 32 | " | " | " | $CH_2OC_2H_5$ | NMR |
| 33 | " | " | " | $CH_2O\text{-}n\text{-}C_3H_7$ | NMR |
| 34 | " | " | " | $CH_2O\text{-}i\text{-}C_3H_7$ | |
| 35 | " | " | " | $CH_2O\text{-}n\text{-}C_4H_9$ | |

TABLE 1-continued

Oxazolines of the formula (I), Z = O, G = 3-isoxazolinyl

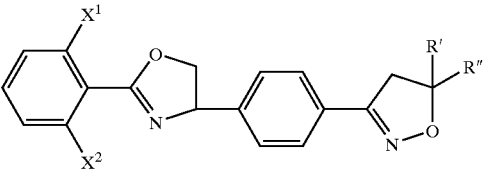

| Ex. No. | $X^1$ | $X^2$ | R' | R" | Physical data |
|---|---|---|---|---|---|
| 36 | " | " | " | $CH_2O\text{-}i\text{-}C_4H_9$ | |
| 37 | " | " | " | $CH_2O\text{-}s\text{-}C_4H_9$ | |
| 38 | " | " | " | $CH_2O\text{-}t\text{-}C_4H_9$ | |
| 39 | " | " | " | $CH_2OCF_2CF_2H$ | NMR |
| 40 | " | " | " | $CH_2OCH_2CF_3$ | NMR |
| 41 | " | " | " | $CH_2O\text{-}phenyl$ | NMR |
| 42 | " | " | " | $CH_2O\text{-}2\text{-}pyridyl$ | |
| 43 | " | " | " | $CF_3$ | NMR |
| 44 | " | " | " | $C_2F_5$ | |
| 45 | " | " | " | $n\text{-}C_3F_7$ | NMR |
| 46 | " | " | " | $n\text{-}C_4F_9$ | NMR |
| 47 | " | " | " | $n\text{-}C_5F_{11}$ | |
| 48 | " | " | " | $n\text{-}C_6F_{13}$ | NMR |
| 50 | " | " | " | 2-F-phenyl | NMR |
| 51 | " | " | " | 3-F-phenyl | NMR |
| 52 | " | " | " | 4-F-phenyl | NMR |
| 53 | " | " | " | 2-Cl-phenyl | |
| 54 | " | " | " | 3-Cl-phenyl | |
| 55 | " | " | " | 4-Cl-phenyl | NMR |
| 56 | " | " | " | 2,4-$Cl_2$-phenyl | |
| 57 | " | " | " | 3,4-$Cl_2$-phenyl | |
| 58 | " | " | " | 2,6-$Cl_2$-phenyl | NMR |
| 59 | " | " | " | 4-Br-phenyl | NMR |
| 60 | " | " | " | 2-$CF_3$-phenyl | NMR |
| 61 | " | " | " | 3-$CF_3$-phenyl | |
| 62 | " | " | " | 3,5-$(CF_3)_2$-phenyl | NMR |
| 63 | " | " | " | 4-$CF_3$-phenyl | NMR |
| 64 | " | " | " | 2-$CH_3$-phenyl | NMR |
| 65 | " | " | " | 4-$CH_3$-phenyl | NMR |
| 66 | " | " | " | 2,4-$(CH_3)_2$-phenyl | NMR |
| 67 | " | " | " | 2,6-$(CH_3)_2$-phenyl | |
| 68 | " | " | " | 2,4,6-$(CH_3)_3$-phenyl | NMR |
| 69 | " | " | " | 2-$CH_3O$-phenyl | |
| 70 | " | " | " | 4-$CH_3O$-phenyl | NMR |
| 71 | " | " | " | 4-$C_2H_5O$-phenyl | |
| 72 | " | " | " | 4-$CF_3O$-phenyl | NMR |
| 73 | " | " | " | 4-CN-phenyl | NMR |
| 74 | " | " | " | 4-t-Bu-phenyl | NMR |
| 75 | " | " | " | 4-$NO_2$-phenyl | |
| 76 | " | " | " | $CH_2$-phenyl | NMR |
| 77 | " | " | " | $CH_2$-(4-F-phenyl) | |
| 78 | " | " | " | $C_2H_4Br$ | NMR |
| 79 | " | " | " | $CH_2SCH_3$ | NMR |
| 80 | " | " | " | $CH_2SOCH_3$ | |
| 81 | " | " | " | $CH_2SO_2CH_3$ | |
| 82 | " | " | " | $CH_2SC_2H_5$ | |
| 83 | " | " | " | $CH_2S\text{-}n\text{-}C_3H_7$ | |
| 84 | " | " | " | $COOCH_3$ | NMR |
| 85 | " | " | " | $COOC_2H_5$ | |
| 86 | " | " | " | $COOCH_2CF_3$ | NMR |
| 87 | " | " | " | $COOC_2H_4CF_3$ | NMR |
| 88 | " | " | " | $C_2F_4Br$ | NMR |
| 89 | " | " | " | $CONHCH_3$ | |
| 90 | " | " | " | $CONHC_2H_5$ | NMR |
| 91 | " | " | " | $CON(CH_3)_2$ | NMR |
| 92 | " | " | " | $CON(C_2H_5)_2$ | |
| 93 | " | " | " | $CONH(n\text{-}C_3H_7)$ | NMR |
| 94 | " | " | " | $CONHCH_2C_2F_5$ | NMR |
| 95 | " | " | " | $CONHCH_2C_2H_3$ | NMR |
| 96 | " | " | " | $CONH\text{-}t\text{-}C_4H_9$ | NMR |
| 97 | " | " | " | $CONH\text{-}n\text{-}C_5H_{11}$ | NMR |
| 98 | " | " | " | $CONHC_3H_6OCH_3$ | NMR |
| 99 | " | " | " | $CONHCH_2C_3F_7$ | NMR |
| 100 | " | " | " | $CONHCH_2$-(2-tetrahydrofuranyl) | NMR |

TABLE 1-continued

Oxazolines of the formula (I), Z = O, G = 3-isoxazolinyl

| Ex. No. | X¹ | X² | R' | R" | Physical data |
|---|---|---|---|---|---|
| 101 | " | " | " | CONH-phenyl | |
| 102 | " | " | " | CONH(4-F-phenyl) | |
| 103 | " | " | " | CONH(4-CF$_3$-phenyl) | NMR |
| 104 | " | " | " | CONCH$_3$(phenyl) | |
| 105 | " | " | " | CONCH$_3$(4-F-phenyl) | |
| 106 | " | " | " | CONH(4-Cl-phenyl) | |
| 107 | " | " | " | CONHC$_2$H$_4$(1-piperidinyl) | NMR |
| 108 | " | " | " | CONHCH$_2$CF$_3$ | NMR |
| 109 | " | " | " | CONHCH$_2$phenyl | |
| 110 | " | " | " | CONHCH$_2$(2,6-F$_2$-phenyl) | NMR |
| 111 | " | " | " | CONHCH$_2$(4-F-phenyl) | |
| 112 | " | " | " | CONHCH$_2$(4-CF$_3$-phenyl) | |
| 113 | " | " | " | CONHCH$_2$(3-CF$_3$-phenyl) | NMR |
| 114 | " | " | " | CH$_2$NHCOCH$_3$ | NMR |
| 115 | " | " | " | CH$_2$NHCOCF$_3$ | NMR |
| 116 | " | " | " | CH$_2$NHCOC$_2$H$_5$ | NMR |
| 117 | " | " | " | CH$_2$NHCOC$_2$F$_5$ | NMR |
| 118 | " | " | " | CH$_2$NHCO-n-C$_3$H$_7$ | |
| 119 | " | " | " | CH$_2$NHCO-i-C$_3$H$_7$ | |
| 120 | " | " | " | CH$_2$NHCO-n-C$_3$F$_7$ | NMR |
| 121 | " | " | " | CH$_2$NHCOC$_2$H$_4$CF$_3$ | NMR |
| 122 | " | " | " | CH$_2$NHCO-t-C$_4$H$_9$ | |
| 123 | " | " | " | CH$_2$NHCOphenyl | |
| 124 | " | " | " | CH$_2$NHCO(4-Cl-phenyl) | NMR |
| 125 | " | " | " | CH$_2$NHCO(2-Cl-5-pyridyl) | NMR |
| 126 | F | H | H | CH$_3$ | |
| 127 | " | " | " | C$_2$H$_5$ | |
| 128 | " | " | " | n-C$_3$H$_7$ | |
| 129 | " | " | " | i-C$_3$H$_7$ | |
| 130 | " | " | " | n-C$_4$H$_9$ | |
| 131 | " | " | " | i-C$_4$H$_9$ | |
| 132 | " | " | " | s-C$_4$H$_9$ | |
| 133 | " | " | " | t-C$_4$H$_9$ | |
| 134 | " | " | " | n-C$_6$H$_{13}$ | |
| 135 | " | " | " | CH$_2$-t-Bu | |
| 136 | " | " | " | CF$_3$ | |
| 137 | " | " | " | C$_2$F$_5$ | |
| 138 | " | " | " | n-C$_3$F$_7$ | |
| 139 | " | " | " | n-C$_4$F$_9$ | NMR |
| 140 | " | " | " | n-C$_5$F$_{11}$ | |
| 141 | " | " | " | n-C$_6$F$_{13}$ | NMR |
| 142 | " | " | " | phenyl | |
| 143 | " | " | " | 2-F-phenyl | |
| 144 | " | " | " | 3-F-phenyl | |
| 145 | " | " | " | 4-F-phenyl | |
| 146 | " | " | " | 2-Cl-phenyl | |
| 147 | " | " | " | 3-Cl-phenyl | |
| 148 | " | " | " | 4-Cl-phenyl | NMR |
| 149 | " | " | " | 2,4-Cl$_2$-phenyl | |
| 150 | " | " | " | 3,4-Cl$_2$-phenyl | |
| 151 | " | " | " | 2,5-Cl$_2$-phenyl | |
| 152 | " | " | " | 2,6-Cl$_2$-phenyl | |
| 153 | " | " | " | 2-CF$_3$-phenyl | |
| 154 | " | " | " | 3-CF$_3$-phenyl | |
| 155 | " | " | " | 3,5-(CF$_3$)$_2$-phenyl | |
| 156 | " | " | " | 4-CF$_3$-phenyl | |
| 157 | " | " | " | 2-CH$_3$-phenyl | |
| 158 | " | " | " | 4-CH$_3$-phenyl | |
| 159 | " | " | " | 2,4-(CH$_3$)$_2$-phenyl | |
| 160 | " | " | " | 2,6-(CH$_3$)$_2$-phenyl | |
| 161 | " | " | " | 2,4,6-(CH$_3$)$_3$-phenyl | |
| 162 | " | " | " | 2-CH$_3$O-phenyl | |
| 163 | " | " | " | 4-CH$_3$O-phenyl | |
| 164 | " | " | " | 4-C$_2$H$_5$O-phenyl | |
| 165 | " | " | " | 4-CF$_3$O-phenyl | |
| 166 | " | " | " | 4-CN-phenyl | |
| 167 | " | " | " | 3-NO$_2$-phenyl | |
| 168 | " | " | " | 4-NO$_2$-phenyl | |
| 169 | F | Cl | H | CH$_3$ | |
| 170 | " | " | " | C$_2$H$_5$ | |
| 171 | " | " | " | n-C$_3$H$_7$ | |
| 172 | " | " | " | i-C$_3$H$_7$ | |
| 173 | " | " | " | n-C$_4$H$_9$ | |
| 174 | " | " | " | i-C$_4$H$_9$ | |
| 175 | " | " | " | s-C$_4$H$_9$ | |
| 176 | " | " | " | t-C$_4$H$_9$ | |
| 177 | " | " | " | n-C$_6$H$_{13}$ | |
| 178 | " | " | " | CH$_2$-t-Bu | |
| 179 | " | " | " | CF$_3$ | |
| 180 | " | " | " | C$_2$F$_5$ | |
| 181 | " | " | " | n-C$_3$F$_7$ | |
| 182 | " | " | " | n-C$_4$F$_9$ | NMR |
| 183 | " | " | " | n-C$_5$F$_{11}$ | |
| 184 | " | " | " | n-C$_6$F$_{13}$ | NMR |
| 185 | " | " | " | phenyl | |
| 186 | " | " | " | 2-F-phenyl | |
| 187 | " | " | " | 3-F-phenyl | |
| 188 | " | " | " | 4-F-phenyl | |
| 189 | " | " | " | 2-Cl-phenyl | |
| 190 | " | " | " | 3-Cl-phenyl | |
| 191 | " | " | " | 4-Cl-phenyl | NMR |
| 192 | " | " | " | 2,4-Cl$_2$-phenyl | |
| 193 | " | " | " | 3,4-Cl$_2$-phenyl | |
| 194 | " | " | " | 2,5-Cl$_2$-phenyl | |
| 195 | " | " | " | 2,6-Cl$_2$-phenyl | |
| 196 | " | " | " | 2-CF$_3$-phenyl | |
| 197 | " | " | " | 3-CF$_3$-phenyl | |
| 198 | " | " | " | 3,5-(CF$_3$)$_2$-phenyl | |
| 199 | " | " | " | 4-CF$_3$-phenyl | |
| 200 | " | " | " | 2-CH$_3$-phenyl | |
| 201 | " | " | " | 4-CH$_3$-phenyl | |
| 202 | " | " | " | 2,4-(CH$_3$)$_2$-phenyl | |
| 203 | " | " | " | 2,6-(CH$_3$)$_2$-phenyl | |
| 204 | " | " | " | 2,4,6-(CH$_3$)$_3$-phenyl | |
| 205 | " | " | " | 2-CH$_3$O-phenyl | NMR |
| 206 | " | " | " | 4-CH$_3$O-phenyl | |
| 207 | " | " | " | 4-C$_2$H$_5$O-phenyl | |
| 208 | " | " | " | 4-CF$_3$O-phenyl | |
| 209 | " | " | " | 4-CN-phenyl | |
| 210 | " | " | " | 3-NO$_2$-phenyl | |
| 211 | " | " | " | 4-NO$_2$-phenyl | |
| 212 | Cl | H | H | CH$_3$ | |
| 213 | " | " | " | C$_2$H$_5$ | |
| 214 | " | " | " | n-C$_3$H$_7$ | |
| 215 | " | " | " | i-C$_3$H$_7$ | |
| 216 | " | " | " | n-C$_4$H$_9$ | |
| 217 | " | " | " | i-C$_4$H$_9$ | |
| 218 | " | " | " | s-C$_4$H$_9$ | |
| 219 | " | " | " | t-C$_4$H$_9$ | |
| 220 | " | " | " | n-C$_6$H$_{13}$ | |
| 221 | " | " | " | CH$_2$-t-Bu | |
| 222 | " | " | " | CF$_3$ | |
| 223 | " | " | " | C$_2$F$_5$ | |
| 224 | " | " | " | n-C$_3$F$_7$ | |
| 225 | " | " | " | n-C$_4$F$_9$ | NMR |
| 226 | " | " | " | n-C$_5$F$_{11}$ | |
| 227 | " | " | " | n-C$_6$F$_{13}$ | NMR |
| 228 | " | " | " | phenyl | |

TABLE 1-continued

Oxazolines of the formula (I), Z = O, G = 3-isoxazolinyl

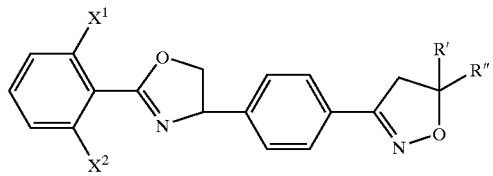

| Ex. No. | X¹ | X² | R' | R" | Physical data |
|---|---|---|---|---|---|
| 229 | " | " | " | 2-F-phenyl | |
| 230 | " | " | " | 3-F-phenyl | |
| 231 | " | " | " | 4-F-phenyl | |
| 232 | " | " | " | 2-Cl-phenyl | |
| 233 | " | " | " | 3-Cl-phenyl | |
| 234 | " | " | " | 4-Cl-phenyl | NMR |
| 235 | " | " | " | 2,4-Cl₂-phenyl | |
| 236 | " | " | " | 3,4-Cl₂-phenyl | |
| 237 | " | " | " | 2,5-Cl₂-phenyl | |
| 238 | " | " | " | 2,6-Cl₂-phenyl | |
| 239 | " | " | " | 2-CF₃-phenyl | |
| 240 | " | " | " | 3-CF₃-phenyl | |
| 241 | " | " | " | 3,5-(CF₃)₂-phenyl | |
| 242 | " | " | " | 4-CF₃-phenyl | |
| 243 | " | " | " | 2-CH₃-phenyl | |
| 244 | " | " | " | 4-CH₃-phenyl | |
| 245 | " | " | " | 2,4-(CH₃)₂-phenyl | |
| 246 | " | " | " | 2,6-(CH₃)₂-phenyl | |
| 247 | " | " | " | 2,4,6-(CH₃)₃-phenyl | |
| 248 | " | " | " | 2-CH₃O-phenyl | |
| 249 | " | " | " | 4-CH₃O-phenyl | |
| 250 | " | " | " | 4-C₂H₅O-phenyl | |
| 251 | " | " | " | 4-CF₃O-phenyl | |
| 252 | " | " | " | 4-CN-phenyl | |
| 253 | " | " | " | 3-NO₂-phenyl | |
| 254 | " | " | " | 4-NO₂-phenyl | |
| 255 | CH₃ | H | H | CH₃ | |
| 256 | " | " | " | C₂H₅ | |
| 257 | " | " | " | n-C₃H₇ | |
| 258 | " | " | " | i-C₃H₇ | |
| 259 | " | " | " | n-C₄H₉ | |
| 260 | " | " | " | i-C₄H₉ | |
| 261 | " | " | " | s-C₄H₉ | |
| 262 | " | " | " | t-C₄H₉ | |
| 263 | " | " | " | n-C₆H₁₃ | |
| 264 | " | " | " | CH₂-t-Bu | |
| 265 | " | " | " | CF₃ | |
| 266 | " | " | " | C₂F₅ | NMR |
| 267 | " | " | " | n-C₃F₇ | |
| 268 | " | " | " | n-C₄F₉ | |
| 269 | " | " | " | n-C₅F₁₁ | |
| 270 | " | " | " | n-C₆F₁₃ | |
| 271 | " | " | " | phenyl | |
| 272 | " | " | " | 2-F-phenyl | |
| 273 | " | " | " | 3-F-phenyl | |
| 274 | " | " | " | 4-F-phenyl | |
| 275 | " | " | " | 2-Cl-phenyl | |
| 276 | " | " | " | 3-Cl-phenyl | |
| 277 | " | " | " | 4-Cl-phenyl | |
| 278 | " | " | " | 2,4-Cl₂-phenyl | |
| 279 | " | " | " | 3,4-Cl₂-phenyl | |
| 280 | " | " | " | 2,5-Cl₂-phenyl | |
| 281 | " | " | " | 2,6-Cl₂-phenyl | |
| 282 | " | " | " | 2-CF₃-phenyl | |
| 283 | " | " | " | 3-CF₃-phenyl | |
| 284 | " | " | " | 3,5-(CF₃)₂-phenyl | |
| 285 | " | " | " | 4-CF₃-phenyl | |
| 286 | " | " | " | 2-CH₃-phenyl | |
| 287 | " | " | " | 4-CH₃-phenyl | |
| 288 | " | " | " | 2,4-(CH₃)₂-phenyl | |
| 289 | " | " | " | 2,6-(CH₃)₂-phenyl | |
| 290 | " | " | " | 2,4,6-(CH₃)₃-phenyl | |
| 291 | " | " | " | 2-CH₃O-phenyl | |
| 292 | " | " | " | 4-CH₃O-phenyl | |
| 293 | " | " | " | 4-C₂H₅O-phenyl | |
| 294 | " | " | " | 4-CF₃O-phenyl | |
| 295 | " | " | " | 4-CN-phenyl | |
| 296 | " | " | " | 3-NO₂-phenyl | |
| 297 | " | " | " | 4-NO₂-phenyl | |
| 298 | Br | H | H | CH₃ | |
| 299 | " | " | " | C₂H₅ | |
| 300 | " | " | " | n-C₃H₇ | |
| 301 | " | " | " | i-C₃H₇ | |
| 302 | " | " | " | n-C₄H₉ | |
| 303 | " | " | " | i-C₄H₉ | |
| 304 | " | " | " | s-C₄H₉ | |
| 305 | " | " | " | t-C₄H₉ | NMR |
| 306 | " | " | " | n-C₆H₁₃ | |
| 307 | " | " | " | CH₂-t-Bu | |
| 308 | " | " | " | CF₃ | |
| 309 | " | " | " | C₂F₅ | |
| 310 | " | " | " | n-C₃F₇ | |
| 311 | " | " | " | n-C₄F₉ | NMR |
| 312 | " | " | " | n-C₅F₁₁ | |
| 313 | " | " | " | n-C₆F₁₃ | NMR |
| 314 | " | " | " | phenyl | |
| 315 | " | " | " | 2-F-phenyl | |
| 316 | " | " | " | 3-F-phenyl | |
| 317 | " | " | " | 4-F-phenyl | |
| 318 | " | " | " | 2-Cl-phenyl | |
| 319 | " | " | " | 3-Cl-phenyl | |
| 320 | " | " | " | 4-Cl-phenyl | |
| 321 | " | " | " | 2,4-Cl₂-phenyl | |
| 322 | " | " | " | 3,4-Cl₂-phenyl | |
| 323 | " | " | " | 2,5-Cl₂-phenyl | |
| 324 | " | " | " | 2,6-Cl₂-phenyl | |
| 325 | " | " | " | 2-CF₃-phenyl | |
| 326 | " | " | " | 3-CF₃-phenyl | |
| 327 | " | " | " | 3,5-(CF₃)₂-phenyl | |
| 328 | " | " | " | 4-CF₃-phenyl | NMR |
| 329 | " | " | " | 2-CH₃-phenyl | |
| 330 | " | " | " | 4-CH₃-phenyl | |
| 331 | " | " | " | 2,4-(CH₃)₂-phenyl | |
| 332 | " | " | " | 2,6-(CH₃)₂-phenyl | |
| 333 | " | " | " | 2,4,6-(CH₃)₃-phenyl | |
| 334 | " | " | " | 2-CH₃O-phenyl | NMR |
| 335 | " | " | " | 4-CH₃O-phenyl | |
| 336 | " | " | " | 4-C₂H₅O-phenyl | |
| 337 | " | " | " | 4-CF₃O-phenyl | |
| 338 | " | " | " | 4-CN-phenyl | |
| 339 | " | " | " | 3-NO₂-phenyl | |
| 340 | " | " | " | 4-NO₂-phenyl | |
| 341 | CH₃ | CH₃ | H | CH₃ | |
| 342 | " | " | " | C₂H₅ | |
| 343 | " | " | " | n-C₃H₇ | |
| 344 | " | " | " | i-C₃H₇ | |
| 345 | " | " | " | n-C₄H₉ | |
| 346 | " | " | " | i-C₄H₉ | |
| 347 | " | " | " | s-C₄H₉ | |
| 348 | " | " | " | t-C₄H₉ | |
| 349 | " | " | " | n-C₆H₁₃ | |
| 350 | " | " | " | CH₂-t-Bu | |
| 351 | " | " | " | CF₃ | |
| 352 | " | " | " | C₂F₅ | |
| 353 | " | " | " | n-C₃F₇ | |
| 354 | " | " | " | n-C₄F₉ | NMR |
| 355 | " | " | " | n-C₅F₁₁ | |
| 356 | " | " | " | n-C₆F₁₃ | NMR |

TABLE 1-continued

Oxazolines of the formula (I), Z = O, G = 3-isoxazolinyl

| Ex. No. | $X^1$ | $X^2$ | R' | R" | Physical data |
|---|---|---|---|---|---|
| 357 | " | " | " | phenyl | |
| 358 | " | " | " | 2-F-phenyl | |
| 359 | " | " | " | 3-F-phenyl | |
| 360 | " | " | " | 4-F-phenyl | |
| 361 | " | " | " | 2-Cl-phenyl | |
| 362 | " | " | " | 3-Cl-phenyl | |
| 363 | " | " | " | 4-Cl-phenyl | NMR |
| 364 | " | " | " | 2,4-$Cl_2$-phenyl | |
| 365 | " | " | " | 3,4-$Cl_2$-phenyl | |
| 366 | " | " | " | 2,5-$Cl_2$-phenyl | |
| 367 | " | " | " | 2,6-$Cl_2$-phenyl | |
| 368 | " | " | " | 2-$CF_3$-phenyl | |
| 369 | " | " | " | 3-$CF_3$-phenyl | |
| 370 | " | " | " | 3,5-$(CF_3)_2$-phenyl | |
| 371 | " | " | " | 4-$CF_3$-phenyl | |
| 372 | " | " | " | 2-$CH_3$-phenyl | |
| 373 | " | " | " | 4-$CH_3$-phenyl | |
| 374 | " | " | " | 2,4-$(CH_3)_2$-phenyl | |
| 375 | " | " | " | 2,6-$(CH_3)_2$-phenyl | |
| 376 | " | " | " | 2,4,6-$(CH_3)_3$-phenyl | |
| 378 | " | " | " | 2-$CH_3O$-phenyl | |
| 379 | " | " | " | 4-$CH_3O$-phenyl | |
| 380 | " | " | " | 4-$C_2H_5O$-phenyl | |
| 381 | " | " | " | 4-$CF_3O$-phenyl | |
| 382 | " | " | " | 4-CN-phenyl | |
| 383 | " | " | " | 3-$NO_2$-phenyl | |
| 384 | " | " | " | 4-$NO_2$-phenyl | |

TABLE 2

Oxazolines, pyrrolines and imidazolines of the formula (I), G = 3-isoxazolinyl

| Ex. No. | $X^1$ | $X^2$ | Z | $R^5$ | Physical data |
|---|---|---|---|---|---|
| 385 | F | F | $CH_2$ | $CH_3$ | |
| 386 | " | " | " | $C_2H_5$ | |
| 387 | " | " | " | n-$C_3H_7$ | |
| 388 | " | " | " | i-$C_3H_7$ | |
| 389 | " | " | " | n-$C_4H_9$ | |
| 390 | " | " | " | i-$C_4H_9$ | |
| 400 | " | " | " | s-$C_4H_9$ | |
| 401 | " | " | " | t-$C_4H_9$ | |
| 402 | " | " | " | n-$C_6H_{13}$ | |
| 403 | " | " | " | $CH_2$-t-Bu | |
| 404 | " | " | " | $CF_3$ | |
| 405 | " | " | " | $C_2F_5$ | |
| 406 | " | " | " | n-$C_3F_7$ | |
| 407 | " | " | " | n-$C_4F_9$ | |
| 408 | " | " | " | n-$C_5F_{11}$ | |
| 409 | " | " | " | n-$C_6F_{13}$ | |
| 410 | " | " | " | phenyl | |
| 411 | " | " | " | 2-F-phenyl | |

TABLE 2-continued

Oxazolines, pyrrolines and imidazolines of the formula (I), G = 3-isoxazolinyl

| Ex. No. | $X^1$ | $X^2$ | Z | $R^5$ | Physical data |
|---|---|---|---|---|---|
| 412 | " | " | " | 3-F-phenyl | |
| 413 | " | " | " | 4-F-phenyl | |
| 414 | " | " | " | 2-Cl-phenyl | |
| 415 | " | " | " | 3-Cl-phenyl | |
| 416 | " | " | " | 4-Cl-phenyl | |
| 417 | " | " | " | 2,4-$Cl_2$-phenyl | |
| 418 | " | " | " | 3,4-$Cl_2$-phenyl | |
| 419 | " | " | " | 2,5-$Cl_2$-phenyl | |
| 420 | " | " | " | 2,6-$Cl_2$-phenyl | |
| 421 | " | " | " | 2-$CF_3$-phenyl | |
| 422 | " | " | " | 3-$CF_3$-phenyl | |
| 423 | " | " | " | 3,5-$(CF_3)_2$-phenyl | |
| 424 | " | " | " | 4-$CF_3$-phenyl | |
| 425 | " | " | " | 2-$CH_3$-phenyl | |
| 426 | " | " | " | 4-$CH_3$-phenyl | |
| 427 | " | " | " | 2,4-$(CH_3)_2$-phenyl | |
| 428 | " | " | " | 2,6-$(CH_3)_2$-phenyl | |
| 429 | " | " | " | 2,4,6-$(CH_3)_3$-phenyl | |
| 430 | " | " | " | 2-$CH_3O$-phenyl | |
| 431 | " | " | " | 4-$CH_3O$-phenyl | |
| 432 | " | " | " | 4-$C_2H_5O$-phenyl | |
| 433 | " | " | " | 4-$CF_3O$-phenyl | |
| 434 | " | " | " | 4-CN-phenyl | |
| 435 | " | " | " | 3-$NO_2$-phenyl | |
| 436 | " | " | " | 4-$NO_2$-phenyl | |
| 437 | F | H | $CH_2$ | $CH_3$ | |
| 438 | " | " | " | $C_2H_5$ | |
| 439 | " | " | " | n-$C_3H_7$ | |
| 440 | " | " | " | i-$C_3H_7$ | |
| 441 | " | " | " | n-$C_4H_9$ | |
| 442 | " | " | " | i-$C_4H_9$ | |
| 443 | " | " | " | s-$C_4H_9$ | |
| 444 | " | " | " | t-$C_4H_9$ | |
| 445 | " | " | " | n-$C_6H_{13}$ | |
| 446 | " | " | " | $CH_2$-t-Bu | |
| 447 | " | " | " | $CF_3$ | |
| 448 | " | " | " | $C_2F_5$ | |
| 449 | " | " | " | n-$C_3F_7$ | |
| 450 | " | " | " | n-$C_4F_9$ | |
| 451 | " | " | " | n-$C_5F_{11}$ | |
| 452 | " | " | " | n-$C_6F_{13}$ | |
| 453 | " | " | " | phenyl | |
| 454 | " | " | " | 2-F-phenyl | |
| 455 | " | " | " | 3-F-phenyl | |
| 456 | " | " | " | 4-F-phenyl | |
| 457 | " | " | " | 2-Cl-phenyl | |
| 458 | " | " | " | 3-Cl-phenyl | |
| 459 | " | " | " | 4-Cl-phenyl | |
| 460 | " | " | " | 2,4-$Cl_2$-phenyl | |
| 461 | " | " | " | 3,4-$Cl_2$-phenyl | |
| 462 | " | " | " | 2,5-$Cl_2$-phenyl | |
| 463 | " | " | " | 2,6-$Cl_2$-phenyl | |
| 464 | " | " | " | 2-$CF_3$-phenyl | |
| 465 | " | " | " | 3-$CF_3$-phenyl | |
| 466 | " | " | " | 3,5-$(CF_3)_2$-phenyl | |
| 467 | " | " | " | 4-$CF_3$-phenyl | |
| 468 | " | " | " | 2-$CH_3$-phenyl | |
| 469 | " | " | " | 4-$CH_3$-phenyl | |
| 470 | " | " | " | 2,4-$(CH_3)_2$-phenyl | |
| 471 | " | " | " | 2,6-$(CH_3)_2$-phenyl | |
| 472 | " | " | " | 2,4,6-$(CH_3)_3$-phenyl | |
| 473 | " | " | " | 2-$CH_3O$-phenyl | |
| 474 | " | " | " | 4-$CH_3O$-phenyl | |
| 475 | " | " | " | 4-$C_2H_5O$-phenyl | |

TABLE 2-continued

Oxazolines, pyrrolines and imidazolines of the formula (I), G = 3-isoxazolinyl

| Ex. No. | X¹ | X² | Z | R⁵ | Physical data |
|---|---|---|---|---|---|
| 476 | " | " | " | 4-CF₃O-phenyl | |
| 477 | " | " | " | 4-CN-phenyl | |
| 478 | " | " | " | 3-NO₂-phenyl | |
| 479 | " | " | " | 4-NO₂-phenyl | |
| 480 | F | Cl | CH₂ | CH₃ | |
| 481 | " | " | " | C₂H₅ | |
| 482 | " | " | " | n-C₃H₇ | |
| 483 | " | " | " | i-C₃H₇ | |
| 484 | " | " | " | n-C₄H₉ | |
| 485 | " | " | " | i-C₄H₉ | |
| 486 | " | " | " | s-C₄H₉ | |
| 487 | " | " | " | t-C₄H₉ | |
| 488 | " | " | " | n-C₆H₁₃ | |
| 489 | " | " | " | CH₂-t-Bu | |
| 490 | " | " | " | CF₃ | |
| 491 | " | " | " | C₂F₅ | |
| 492 | " | " | " | n-C₃F₇ | |
| 493 | " | " | " | n-C₄F₉ | |
| 494 | " | " | " | n-C₅F₁₁ | |
| 495 | " | " | " | n-C₆F₁₃ | |
| 496 | " | " | " | phenyl | |
| 497 | " | " | " | 2-F-phenyl | |
| 498 | " | " | " | 3-F-phenyl | |
| 499 | " | " | " | 4-F-phenyl | |
| 500 | " | " | " | 2-Cl-phenyl | |
| 501 | " | " | " | 3-Cl-phenyl | |
| 502 | " | " | " | 4-Cl-phenyl | |
| 503 | " | " | " | 2,4-Cl₂-phenyl | |
| 504 | " | " | " | 3,4-Cl₂-phenyl | |
| 505 | " | " | " | 2,5-Cl₂-phenyl | |
| 506 | " | " | " | 2,6-Cl₂-phenyl | |
| 507 | " | " | " | 2-CF₃-phenyl | |
| 508 | " | " | " | 3-CF₃-phenyl | |
| 509 | " | " | " | 3,5-(CF₃)₂-phenyl | |
| 510 | " | " | " | 4-CF₃-phenyl | |
| 511 | " | " | " | 2-CH₃-phenyl | |
| 512 | " | " | " | 4-CH₃-phenyl | |
| 513 | " | " | " | 2,4-(CH₃)₂-phenyl | |
| 514 | " | " | " | 2,6-(CH₃)₂-phenyl | |
| 515 | " | " | " | 2,4,6-(CH₃)₃-phenyl | |
| 516 | " | " | " | 2-CH₃O-phenyl | |
| 517 | " | " | " | 4-CH₃O-phenyl | |
| 518 | " | " | " | 4-C₂H₅O-phenyl | |
| 519 | " | " | " | 4-CF₃O-phenyl | |
| 520 | " | " | " | 4-CN-phenyl | |
| 521 | " | " | " | 3-NO₂-phenyl | |
| 522 | " | " | " | 4-NO₂-phenyl | |
| 523 | F | F | NCOOEt | CH₃ | |
| 524 | " | " | " | C₂H₅ | |
| 525 | " | " | " | n-C₃H₇ | |
| 526 | " | " | " | i-C₃H₇ | |
| 527 | " | " | " | n-C₄H₉ | |
| 528 | " | " | " | i-C₄H₉ | |
| 529 | " | " | " | s-C₄H₉ | |
| 530 | " | " | " | t-C₄H₉ | |
| 531 | " | " | " | n-C₆H₁₃ | |
| 532 | " | " | " | CH₂-t-Bu | |
| 533 | " | " | " | CF₃ | |
| 534 | " | " | " | C₂F₅ | |
| 535 | " | " | " | n-C₃F₇ | |
| 536 | " | " | " | n-C₄F₉ | |
| 537 | " | " | " | n-C₅F₁₁ | |
| 538 | " | " | " | n-C₆F₁₃ | |
| 539 | " | " | " | phenyl | |
| 540 | " | " | " | 2-F-phenyl | |
| 541 | " | " | " | 3-F-phenyl | |
| 542 | " | " | " | 4-F-phenyl | |
| 543 | " | " | " | 2-Cl-phenyl | |
| 544 | " | " | " | 3-Cl-phenyl | |
| 545 | " | " | " | 4-Cl-phenyl | |
| 546 | " | " | " | 2,4-Cl₂-phenyl | |
| 547 | " | " | " | 3,4-Cl₂-phenyl | |
| 548 | " | " | " | 2,5-Cl₂-phenyl | |
| 549 | " | " | " | 2,6-Cl₂-phenyl | |
| 550 | " | " | " | 2-CF₃-phenyl | |
| 551 | " | " | " | 3-CF₃-phenyl | |
| 552 | " | " | " | 3,5-(CF₃)₂-phenyl | |
| 553 | " | " | " | 4-CF₃-phenyl | |
| 554 | " | " | " | 2-CH₃-phenyl | |
| 555 | " | " | " | 4-CH₃-phenyl | |
| 556 | " | " | " | 2,4-(CH₃)₂-phenyl | |
| 557 | " | " | " | 2,6-(CH₃)₂-phenyl | |
| 558 | " | " | " | 2,4,6-(CH₃)₃-phenyl | |
| 559 | " | " | " | 2-CH₃O-phenyl | |
| 560 | " | " | " | 4-CH₃O-phenyl | |
| 561 | " | " | " | 4-C₂H₅O-phenyl | |
| 562 | " | " | " | 4-CF₃O-phenyl | |
| 563 | " | " | " | 4-CN-phenyl | |
| 564 | " | " | " | 3-NO₂-phenyl | |
| 565 | " | " | " | 4-NO₂-phenyl | |

TABLE 3

Oxazolines of the formula (I), Z = O, G = 5-isoxazolinyl

| Ex. No. | X¹ | X² | R⁵ | Physical data |
|---|---|---|---|---|
| 566 | F | F | CH₃ | NMR |
| 567 | " | " | C₂H₅ | NMR |
| 568 | " | " | n-C₃H₇ | NMR |
| 569 | " | " | i-C₃H₇ | NMR |
| 570 | " | " | n-C₄H₉ | NMR |
| 571 | " | " | i-C₄H₉ | |
| 572 | " | " | s-C₄H₉ | |
| 573 | " | " | t-C₄H₉ | NMR |
| 574 | " | " | n-C₅H₁₁ | NMR |
| 575 | " | " | n-C₆H₁₃ | |
| 576 | " | " | CH(C₂H₅)₂ | NMR |
| 577 | " | " | CH₂-t-Bu | |
| 578 | " | " | CH₂CF₃ | NMR |
| 579 | " | " | C₂H₄CF₃ | NMR |
| 580 | " | " | CF₃ | |
| 581 | " | " | C₂F₅ | |
| 582 | " | " | n-C₃F₇ | |
| 583 | " | " | n-C₄F₉ | |

TABLE 3-continued

Oxazolines of the formula (I), Z = O, G = 5-isoxazolinyl

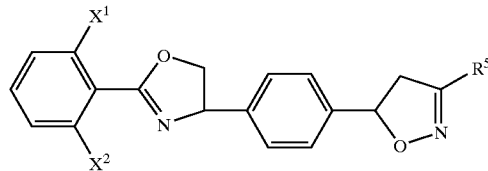
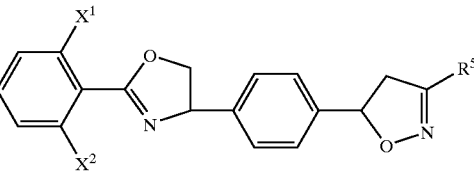

| Ex. No. | $X^1$ | $X^2$ | $R^5$ | Physical data |
|---|---|---|---|---|
| 584 | " | " | n-$C_5F_{11}$ | |
| 585 | " | " | n-$C_6F_{13}$ | |
| 586 | " | " | phenyl | |
| 587 | " | " | 2-F-phenyl | |
| 588 | " | " | 3-F-phenyl | |
| 589 | " | " | 4-F-phenyl | NMR |
| 590 | " | " | 2-Cl-phenyl | |
| 591 | " | " | 3-Cl-phenyl | |
| 592 | " | " | 4-Cl-phenyl | NMR |
| 593 | " | " | 2,4-$Cl_2$-phenyl | |
| 594 | " | " | 3,4-$Cl_2$-phenyl | |
| 595 | " | " | 2,5-$Cl_2$-phenyl | |
| 596 | " | " | 2,6-$Cl_2$-phenyl | |
| 597 | " | " | 2-$CF_3$-phenyl | |
| 598 | " | " | 3-$CF_3$-phenyl | |
| 599 | " | " | 3,5-$(CF_3)_2$-phenyl | |
| 600 | " | " | 4-$CF_3$-phenyl | NMR |
| 601 | " | " | 2-$CH_3$-phenyl | |
| 602 | " | " | 4-$CH_3$-phenyl | |
| 603 | " | " | 2,4-$(CH_3)_2$-phenyl | |
| 604 | " | " | 2,6-$(CH_3)_2$-phenyl | |
| 605 | " | " | 2,4,6-$(CH_3)_3$-phenyl | NMR |
| 606 | " | " | 2-$CH_3O$-phenyl | |
| 607 | " | " | 4-$CH_3O$-phenyl | |
| 608 | " | " | 4-$C_2H_5O$-phenyl | |
| 609 | " | " | 4-$CF_3O$-phenyl | |
| 610 | " | " | 4-CN-phenyl | |
| 611 | " | " | 3-$NO_2$-phenyl | |
| 612 | " | " | 4-$NO_2$-phenyl | |
| 613 | " | " | COOH | NMR |
| 614 | " | " | $COOC_2H_5$ | NMR |
| 615 | " | " | $COOCH_2CF_3$ | NMR |
| 616 | " | " | $COOC_2H_4CF_3$ | NMR |
| 617 | " | " | $CONH_2$ | |
| 618 | " | " | $CONHCH_3$ | |
| 619 | " | " | $CONHC_2H_5$ | NMR |
| 620 | " | " | $CON(CH_3)_2$ | |
| 621 | " | " | $CON(C_2H_5)_2$ | NMR |
| 622 | " | " | CONH(n-$C_3H_7$) | NMR |
| 623 | " | " | $CONHCH_2C_2F_5$ | NMR |
| 624 | " | " | CONH-t-$C_4H_9$ | NMR |
| 625 | " | " | $CONHCH_2C_2H_3$ | NMR |
| 626 | " | " | $CONHCH_2C_3F_7$ | NMR |
| 627 | " | " | CONH-s-$C_5H_{11}$ | NMR |
| 628 | " | " | $CONHCH_2CF_3$ | NMR |
| 629 | " | " | $CONHC_3H_6OCH_3$ | NMR |
| 630 | " | " | $CONHCH_2$-(2-tetrahydrofuranyl) | NMR |
| 631 | " | " | $CONHCH_2$-(2,6-$F_2$-phenyl) | NMR |
| 632 | " | " | $CONHCH_2$-(4-F-phenyl) | |
| 633 | " | " | $CONHCH_2$-(3-$CF_3$-phenyl) | NMR |
| 634 | " | " | $CONHCH_2$-(4-$CF_3$-phenyl) | |
| 635 | " | " | CONH(2,5-$F_2$-phenyl) | |
| 636 | " | " | CONH(4-F-phenyl) | |
| 637 | " | " | CONH(3-$CF_3$-phenyl) | |
| 638 | " | " | CONH(4-$CF_3$-phenyl) | |
| 639 | F | H | $CH_3$ | |
| 640 | " | " | $C_2H_5$ | |
| 641 | " | " | n-$C_3H_7$ | |
| 642 | " | " | i-$C_3H_7$ | |
| 643 | " | " | n-$C_4H_9$ | |
| 644 | " | " | i-$C_4H_9$ | |
| 645 | " | " | s-$C_4H_9$ | |
| 646 | " | " | t-$C_4H_9$ | |
| 647 | " | " | n-$C_5H_{11}$ | |
| 648 | " | " | n-$C_6H_{13}$ | |
| 649 | " | " | $CH(C_2H_5)_2$ | |
| 650 | " | " | $CH_2$-t-Bu | |
| 651 | " | " | $CH_2CF_3$ | |
| 652 | " | " | $C_2H_4CF_3$ | |
| 653 | " | " | $CF_3$ | |
| 654 | " | " | $C_2F_5$ | |
| 655 | " | " | n-$C_3F_7$ | |
| 656 | " | " | n-$C_4F_9$ | |
| 657 | " | " | n-$C_5F_{11}$ | |
| 658 | " | " | n-$C_6F_{13}$ | |
| 659 | " | " | phenyl | |
| 660 | " | " | 2-F-phenyl | |
| 661 | " | " | 3-F-phenyl | |
| 662 | " | " | 4-F-phenyl | |
| 663 | " | " | 2-Cl-phenyl | |
| 664 | " | " | 3-Cl-phenyl | |
| 665 | " | " | 4-Cl-phenyl | |
| 666 | " | " | 2,4-$Cl_2$-phenyl | |
| 667 | " | " | 3,4-$Cl_2$-phenyl | |
| 668 | " | " | 2,5-$Cl_2$-phenyl | |
| 669 | " | " | 2,6-$Cl_2$-phenyl | |
| 670 | " | " | 2-$CF_3$-phenyl | |
| 671 | " | " | 3-$CF_3$-phenyl | |
| 672 | " | " | 3,5-$(CF_3)_2$-phenyl | |
| 673 | " | " | 4-$CF_3$-phenyl | |
| 674 | " | " | 2-$CH_3$-phenyl | |
| 675 | " | " | 4-$CH_3$-phenyl | |
| 676 | " | " | 2,4-$(CH_3)_2$-phenyl | |
| 677 | " | " | 2,6-$(CH_3)_2$-phenyl | |
| 678 | " | " | 2,4,6-$(CH_3)_3$-phenyl | |
| 679 | " | " | 2-$CH_3O$-phenyl | |
| 680 | " | " | 4-$CH_3O$-phenyl | |
| 681 | " | " | 4-$C_2H_5O$-phenyl | |
| 682 | " | " | 4-$CF_3O$-phenyl | |
| 683 | " | " | 4-CN-phenyl | |
| 684 | " | " | 3-$NO_2$-phenyl | |
| 685 | " | " | 4-$NO_2$-phenyl | |
| 686 | F | H | $CH_3$ | |
| 687 | " | " | $C_2H_5$ | |
| 688 | " | " | n-$C_3H_7$ | |
| 689 | " | " | i-$C_3H_7$ | |
| 690 | " | " | n-$C_4H_9$ | |
| 691 | " | " | i-$C_4H_9$ | |
| 692 | " | " | S-$C_4H_9$ | |
| 693 | " | " | t-$C_4H_9$ | |
| 694 | " | " | n-$C_5H_{11}$ | |
| 695 | " | " | n-$C_6H_{13}$ | |
| 696 | " | " | $CH(C_2H_5)_2$ | |
| 697 | " | " | $CH_2$-t-Bu | |
| 698 | " | " | $CH_2CF_3$ | |
| 699 | " | " | $C_2H_4CF_3$ | |
| 700 | " | " | $CF_3$ | |
| 701 | " | " | $C_2F_5$ | |
| 702 | " | " | n-$C_3F_7$ | |
| 703 | " | " | n-$C_4F_9$ | |
| 704 | " | " | n-$C_5F_{11}$ | |
| 705 | " | " | n-$C_6F_{13}$ | |
| 706 | " | " | phenyl | |
| 707 | " | " | 2-F-phenyl | |
| 708 | " | " | 3-F-phenyl | |
| 709 | " | " | 4-F-phenyl | |
| 710 | " | " | 2-Cl-phenyl | |
| 711 | " | " | 3-Cl-phenyl | |

TABLE 3-continued

Oxazolines of the formula (I), Z = O, G = 5-isoxazolinyl

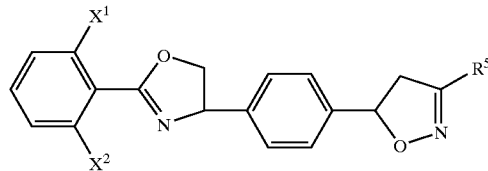

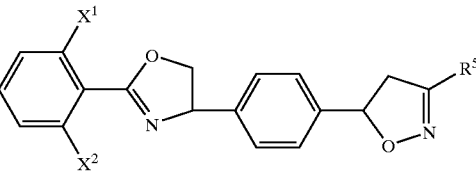

| Ex. No. | $X^1$ | $X^2$ | $R^5$ | Physical data |
|---|---|---|---|---|
| 712 | " | " | 4-Cl-phenyl | |
| 713 | " | " | 2,4-Cl$_2$-phenyl | |
| 714 | " | " | 3,4-Cl$_2$-phenyl | |
| 715 | " | " | 2,5-Cl$_2$-phenyl | |
| 716 | " | " | 2,6-Cl$_2$-phenyl | |
| 717 | " | " | 2-CF$_3$-phenyl | |
| 718 | " | " | 3-CF$_3$-phenyl | |
| 719 | " | " | 3,5-(CF$_3$)$_2$-phenyl | |
| 720 | " | " | 4-CF$_3$-phenyl | |
| 721 | " | " | 2-CH$_3$-phenyl | |
| 722 | " | " | 4-CH$_3$-phenyl | |
| 723 | " | " | 2,4-(CH$_3$)$_2$-phenyl | |
| 724 | " | " | 2,6-(CH$_3$)$_2$-phenyl | |
| 725 | " | " | 2,4,6-(CH$_3$)$_3$-phenyl | |
| 726 | " | " | 2-CH$_3$O-phenyl | |
| 727 | " | " | 4-CH$_3$O-phenyl | |
| 728 | " | " | 4-C$_2$H$_5$O-phenyl | |
| 729 | " | " | 4-CF$_3$O-phenyl | |
| 730 | " | " | 4-CN-phenyl | |
| 731 | " | " | 3-NO$_2$-phenyl | |
| 732 | " | " | 4-NO$_2$-phenyl | |
| 733 | Cl | H | CH$_3$ | |
| 734 | " | " | C$_2$H$_5$ | |
| 735 | " | " | n-C$_3$H$_7$ | |
| 736 | " | " | i-C$_3$H$_7$ | |
| 737 | " | " | n-C$_4$H$_9$ | |
| 738 | " | " | i-C$_4$H$_9$ | |
| 739 | " | " | s-C$_4$H$_9$ | |
| 740 | " | " | t-C$_4$H$_9$ | |
| 741 | " | " | n-C$_5$H$_{13}$ | |
| 742 | " | " | n-C$_6$H$_{13}$ | |
| 743 | " | " | CH(C$_2$H$_5$)$_2$ | |
| 744 | " | " | CH$_2$-t-Bu | |
| 745 | " | " | CH$_2$CF$_3$ | |
| 746 | " | " | C$_2$H$_4$CF$_3$ | |
| 747 | " | " | CF$_3$ | |
| 748 | " | " | C$_2$F$_5$ | |
| 749 | " | " | n-C$_3$F$_7$ | |
| 750 | " | " | n-C$_4$F$_9$ | |
| 751 | " | " | n-C$_5$F$_{11}$ | |
| 752 | " | " | n-C$_6$F$_{13}$ | |
| 753 | " | " | phenyl | |
| 754 | " | " | 2-F-phenyl | |
| 755 | " | " | 3-F-phenyl | |
| 756 | " | " | 4-F-phenyl | |
| 757 | " | " | 2-Cl-phenyl | |
| 758 | " | " | 3-Cl-phenyl | |
| 759 | " | " | 4-Cl-phenyl | |
| 760 | " | " | 2,4-Cl$_2$-phenyl | |
| 761 | " | " | 3,4-Cl$_2$-phenyl | |
| 762 | " | " | 2,5-Cl$_2$-phenyl | |
| 763 | " | " | 2,6-Cl$_2$-phenyl | |
| 764 | " | " | 2-CF$_3$-phenyl | |
| 765 | " | " | 3-CF$_3$-phenyl | |
| 767 | " | " | 3,5-(CF$_3$)$_2$-phenyl | |
| 768 | " | " | 4-CF$_3$-phenyl | |
| 769 | " | " | 2-CH$_3$-phenyl | |
| 770 | " | " | 4-CH$_3$-phenyl | |
| 771 | " | " | 2,4-(CH$_3$)$_2$-phenyl | |
| 772 | " | " | 2,6-(CH$_3$)$_2$-phenyl | |
| 773 | " | " | 2,4,6-(CH$_3$)$_3$-phenyl | |
| 774 | " | " | 2-CH$_3$O-phenyl | |
| 776 | " | " | 4-CH$_3$O-phenyl | |
| 777 | " | " | 4-C$_2$H$_5$O-phenyl | |
| 778 | " | " | 4-CF$_3$O-phenyl | |
| 779 | " | " | 4-CN-phenyl | |
| 780 | " | " | 3-NO$_2$-phenyl | |
| 781 | " | " | 4-NO$_2$-phenyl | |
| 782 | CH$_3$ | H | CH$_3$ | |
| 783 | " | " | C$_2$H$_5$ | |
| 784 | " | " | n-C$_3$H$_7$ | |
| 785 | " | " | i-C$_3$H$_7$ | |
| 786 | " | " | n-C$_4$H$_9$ | |
| 787 | " | " | i-C$_4$H$_9$ | |
| 788 | " | " | s-C$_4$H$_9$ | |
| 789 | " | " | t-C$_4$H$_9$ | |
| 790 | " | " | n-C$_5$H$_{11}$ | |
| 791 | " | " | n-C$_6$H$_{13}$ | |
| 792 | " | " | CH(C$_2$H$_5$)$_2$ | |
| 793 | " | " | CH$_2$-t-Bu | |
| 794 | " | " | CH$_2$CF$_3$ | |
| 795 | " | " | C$_2$H$_4$CF$_3$ | |
| 796 | " | " | CF$_3$ | |
| 797 | " | " | C$_2$F$_5$ | |
| 798 | " | " | n-C$_3$F$_7$ | |
| 799 | " | " | n-C$_4$F$_9$ | |
| 800 | " | " | n-C$_5$F$_{11}$ | |
| 801 | " | " | n-C$_6$F$_{13}$ | |
| 802 | " | " | phenyl | |
| 803 | " | " | 2-F-phenyl | |
| 804 | " | " | 3-F-phenyl | |
| 805 | " | " | 4-F-phenyl | |
| 806 | " | " | 2-Cl-phenyl | |
| 807 | " | " | 3-Cl-phenyl | |
| 808 | " | " | 4-Cl-phenyl | |
| 809 | " | " | 2,4-Cl$_2$-phenyl | |
| 810 | " | " | 3,4-Cl$_2$-phenyl | |
| 811 | " | " | 2,5-Cl$_2$-phenyl | |
| 812 | " | " | 2,6-Cl$_2$-phenyl | |
| 813 | " | " | 2-CF$_3$-phenyl | |
| 814 | " | " | 3-CF$_3$-phenyl | |
| 815 | " | " | 3,5-(CF$_3$)$_2$-phenyl | |
| 816 | " | " | 4-CF$_3$-phenyl | |
| 817 | " | " | 2-CH$_3$-phenyl | |
| 818 | " | " | 4-CH$_3$-phenyl | |
| 819 | " | " | 2,4-(CH$_3$)$_2$-phenyl | |
| 820 | " | " | 2,6-(CH$_3$)$_2$-phenyl | |
| 821 | " | " | 2,4,6-(CH$_3$)$_3$-phenyl | |
| 822 | " | " | 2-CH$_3$O-phenyl | |
| 823 | " | " | 4-CH$_3$O-phenyl | |
| 824 | " | " | 4-C$_2$H$_5$O-phenyl | |
| 825 | " | " | 4-CF$_3$O-phenyl | |
| 826 | " | " | 4-CN-phenyl | |
| 827 | " | " | 3-NO$_2$-phenyl | |
| 828 | " | " | 4-NO$_2$-phenyl | |
| 829 | Br | H | CH$_3$ | |
| 830 | " | " | C$_2$H$_5$ | |
| 831 | " | " | n-C$_3$H$_7$ | |
| 832 | " | " | i-C$_3$H$_7$ | |
| 833 | " | " | n-C$_4$H$_9$ | |
| 834 | " | " | i-C$_4$H$_9$ | |
| 835 | " | " | s-C$_4$H$_9$ | |
| 836 | " | " | t-C$_4$H$_9$ | |
| 837 | " | " | n-C$_5$H$_{11}$ | |
| 838 | " | " | n-C$_6$H$_{13}$ | |
| 839 | " | " | CH(C$_2$H$_5$)$_2$ | |
| 840 | " | " | CH$_2$-t-Bu | |
| 841 | " | " | CH$_2$CF$_3$ | |

TABLE 3-continued

Oxazolines of the formula (I), Z = O, G = 5-isoxazolinyl

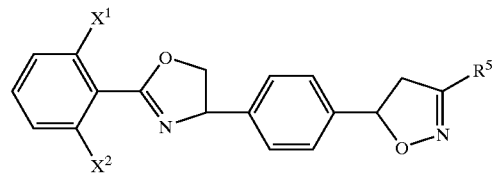

| Ex. No. | $X^1$ | $X^2$ | $R^5$ | Physical data |
|---|---|---|---|---|
| 842 | " | " | $C_2H_4CF_3$ | |
| 843 | " | " | $CF_3$ | |
| 844 | " | " | $C_2F_5$ | |
| 845 | " | " | $n$-$C_3F_7$ | |
| 846 | " | " | $n$-$C_4F_9$ | |
| 847 | " | " | $n$-$C_5F_{11}$ | |
| 848 | " | " | $n$-$C_6F_{13}$ | |
| 849 | " | " | phenyl | |
| 850 | " | " | 2-F-phenyl | |
| 851 | " | " | 3-F-phenyl | |
| 852 | " | " | 4-F-phenyl | |
| 853 | " | " | 2-Cl-phenyl | |
| 854 | " | " | 3-Cl-phenyl | |
| 855 | " | " | 4-Cl-phenyl | |
| 856 | " | " | 2,4-$Cl_2$-phenyl | |
| 857 | " | " | 3,4-$Cl_2$-phenyl | |
| 858 | " | " | 2,5-$Cl_2$-phenyl | |
| 859 | " | " | 2,6-$Cl_2$-phenyl | |
| 860 | " | " | 2-$CF_3$-phenyl | |
| 861 | " | " | 3-$CF_3$-phenyl | |
| 862 | " | " | 3,5-$(CF_3)_2$-phenyl | |
| 863 | " | " | 4-$CF_3$-phenyl | |
| 864 | " | " | 2-$CH_3$-phenyl | |
| 865 | " | " | 4-$CH_3$-phenyl | |
| 866 | " | " | 2,4-$(CH_3)_2$-phenyl | |
| 867 | " | " | 2,6-$(CH_3)_2$-phenyl | |
| 868 | " | " | 2,4,6-$(CH_3)_3$-phenyl | |
| 869 | " | " | 2-$CH_3O$-phenyl | |
| 870 | " | " | 4-$CH_3O$-phenyl | |
| 871 | " | " | 4-$C_2H_5O$-phenyl | |
| 872 | " | " | 4-$CF_3O$-phenyl | |
| 873 | " | " | 4-CN-phenyl | |
| 874 | " | " | 3-$NO_2$-phenyl | |
| 875 | " | " | 4-$NO_2$-phenyl | |

TABLE 4

Pyrrolines and imidazolines of the formula (I), G = 5-isoxazolinyl

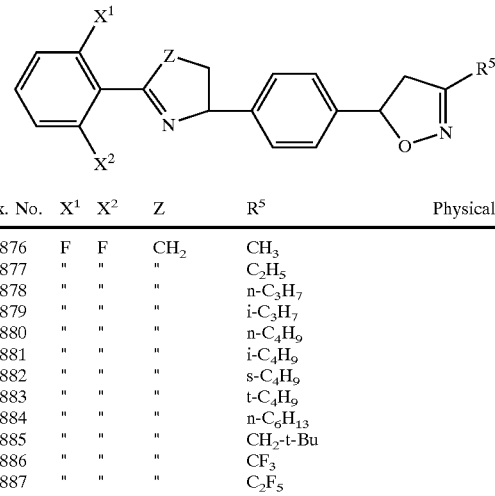

| Ex. No. | $X^1$ | $X^2$ | Z | $R^5$ | Physical data |
|---|---|---|---|---|---|
| 876 | F | F | $CH_2$ | $CH_3$ | |
| 877 | " | " | " | $C_2H_5$ | |
| 878 | " | " | " | $n$-$C_3H_7$ | |
| 879 | " | " | " | $i$-$C_3H_7$ | |
| 880 | " | " | " | $n$-$C_4H_9$ | |
| 881 | " | " | " | $i$-$C_4H_9$ | |
| 882 | " | " | " | $s$-$C_4H_9$ | |
| 883 | " | " | " | $t$-$C_4H_9$ | |
| 884 | " | " | " | $n$-$C_6H_{13}$ | |
| 885 | " | " | " | $CH_2$-$t$-Bu | |
| 886 | " | " | " | $CF_3$ | |
| 887 | " | " | " | $C_2F_5$ | |
| 888 | " | " | " | $n$-$C_3F_7$ | |
| 889 | " | " | " | $n$-$C_4F_9$ | |
| 890 | " | " | " | $n$-$C_5F_{11}$ | |
| 891 | " | " | " | $n$-$C_6F_{13}$ | |
| 892 | " | " | " | phenyl | |
| 893 | " | " | " | 2-F-phenyl | |
| 894 | " | " | " | 3-F-phenyl | |
| 895 | " | " | " | 4-F-phenyl | |
| 896 | " | " | " | 2-Cl-phenyl | |
| 897 | " | " | " | 3-Cl-phenyl | |
| 898 | " | " | " | 4-Cl-phenyl | |
| 899 | " | " | " | 2,4-$Cl_2$-phenyl | |
| 900 | " | " | " | 3,4-$Cl_2$-phenyl | |
| 901 | " | " | " | 2,5-$Cl_2$-phenyl | |
| 902 | " | " | " | 2,6-$Cl_2$-phenyl | |
| 903 | " | " | " | 2-$CF_3$-phenyl | |
| 904 | " | " | " | 3-$CF_3$-phenyl | |
| 905 | " | " | " | 3,5-$(CF_3)_2$-phenyl | |
| 906 | " | " | " | 4-$CF_3$-phenyl | |
| 907 | " | " | " | 2-$CH_3$-phenyl | |
| 908 | " | " | " | 4-$CH_3$-phenyl | |
| 909 | " | " | " | 2,4-$(CH_3)_2$-phenyl | |
| 910 | " | " | " | 2,6-$(CH_3)_2$-phenyl | |
| 911 | " | " | " | 2,4,6-$(CH_3)_3$-phenyl | |
| 912 | " | " | " | 2-$CH_3O$-phenyl | |
| 913 | " | " | " | 4-$CH_3O$-phenyl | |
| 914 | " | " | " | 4-$C_2H_5O$-phenyl | |
| 915 | " | " | " | 4-$CF_3O$-phenyl | |
| 916 | " | " | " | 4-CN-phenyl | |
| 917 | " | " | " | 3-$NO_2$-phenyl | |
| 918 | " | " | " | 4-$NO_2$-phenyl | |
| 919 | F | H | $CH_2$ | $CH_3$ | |
| 920 | " | " | " | $C_2H_5$ | |
| 921 | " | " | " | $n$-$C_3H_7$ | |
| 922 | " | " | " | $i$-$C_3H_7$ | |
| 923 | " | " | " | $n$-$C_4H_9$ | |
| 924 | " | " | " | $i$-$C_4H_9$ | |
| 925 | " | " | " | $s$-$C_4H_9$ | |
| 926 | " | " | " | $t$-$C_4H_9$ | |
| 927 | " | " | " | $n$-$C_6H_{13}$ | |
| 928 | " | " | " | $CH_2$-$t$-Bu | |
| 929 | " | " | " | $CF_3$ | |
| 930 | " | " | " | $C_2F_5$ | |
| 931 | " | " | " | $n$-$C_3F_7$ | |
| 932 | " | " | " | $n$-$C_4F_9$ | |
| 933 | " | " | " | $n$-$C_5F_{11}$ | |
| 934 | " | " | " | $n$-$C_6F_{13}$ | |
| 935 | " | " | " | phenyl | |
| 936 | " | " | " | 2-F-phenyl | |
| 937 | " | " | " | 3-F-phenyl | |
| 938 | " | " | " | 4-F-phenyl | |
| 939 | " | " | " | 2-Cl-phenyl | |
| 940 | " | " | " | 3-Cl-phenyl | |
| 941 | " | " | " | 4-Cl-phenyl | |
| 942 | " | " | " | 2,4-$Cl_2$-phenyl | |
| 943 | " | " | " | 3,4-$Cl_2$-phenyl | |
| 944 | " | " | " | 2,5-$Cl_2$-phenyl | |
| 945 | " | " | " | 2,6-$Cl_2$-phenyl | |
| 946 | " | " | " | 2-$CF_3$-phenyl | |
| 947 | " | " | " | 3-$CF_3$-phenyl | |
| 948 | " | " | " | 3,5-$(CF_3)_2$-phenyl | |
| 949 | " | " | " | 4-$CF_3$-phenyl | |
| 950 | " | " | " | 2-$CH_3$-phenyl | |
| 951 | " | " | " | 4-$CH_3$-phenyl | |
| 952 | " | " | " | 2,4-$(CH_3)_2$-phenyl | |

TABLE 4-continued

Pyrrolines and imidazolines of the formula (I), G = 5-isoxazolinyl

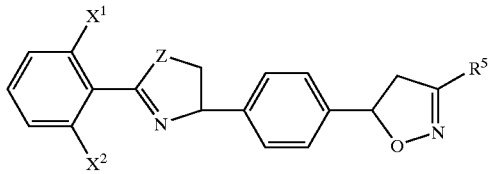

| Ex. No. | X¹ | X² | Z | R⁵ | Physical data |
|---|---|---|---|---|---|
| 953 | " | " | " | 2,6-(CH₃)₂-phenyl | |
| 954 | " | " | " | 2,4,6-(CH₃)₃-phenyl | |
| 955 | " | " | " | 2-CH₃O-phenyl | |
| 956 | " | " | " | 4-CH₃O-phenyl | |
| 957 | " | " | " | 4-C₂H₅O-phenyl | |
| 958 | " | " | " | 4-CF₃O-phenyl | |
| 959 | " | " | " | 4-CN-phenyl | |
| 960 | " | " | " | 3-NO₂-phenyl | |
| 961 | " | " | " | 4-NO₂-phenyl | |
| 962 | F | Cl | CH₂ | CH₃ | |
| 963 | " | " | " | C₂H₅ | |
| 964 | " | " | " | n-C₃H₇ | |
| 965 | " | " | " | i-C₃H₇ | |
| 966 | " | " | " | n-C₄H₉ | |
| 967 | " | " | " | i-C₄H₉ | |
| 968 | " | " | " | s-C₄H₉ | |
| 969 | " | " | " | t-C₄H₉ | |
| 970 | " | " | " | n-C₆H₁₃ | |
| 971 | " | " | " | CH₂-t-Bu | |
| 972 | " | " | " | CF₃ | |
| 973 | " | " | " | C₂F₅ | |
| 974 | " | " | " | n-C₃F₇ | |
| 975 | " | " | " | n-C₄F₉ | |
| 976 | " | " | " | n-C₅F₁₁ | |
| 977 | " | " | " | n-C₆F₁₃ | |
| 978 | " | " | " | phenyl | |
| 979 | " | " | " | 2-F-phenyl | |
| 980 | " | " | " | 3-F-phenyl | |
| 981 | " | " | " | 4-F-phenyl | |
| 982 | " | " | " | 2-Cl-phenyl | |
| 983 | " | " | " | 3-Cl-phenyl | |
| 984 | " | " | " | 4-Cl-phenyl | |
| 985 | " | " | " | 2,4-Cl₂-phenyl | |
| 986 | " | " | " | 3,4-Cl₂-phenyl | |
| 987 | " | " | " | 2,5-Cl₂-phenyl | |
| 988 | " | " | " | 2,6-Cl₂-phenyl | |
| 989 | " | " | " | 2-CF₃-phenyl | |
| 990 | " | " | " | 3-CF₃-phenyl | |
| 991 | " | " | " | 3,5-(CF₃)₂-phenyl | |
| 992 | " | " | " | 4-CF₃-phenyl | |
| 993 | " | " | " | 2-CH₃-phenyl | |
| 994 | " | " | " | 4-CH₃-phenyl | |
| 995 | " | " | " | 2,4-(CH₃)₂-phenyl | |
| 996 | " | " | " | 2,6-(CH₃)₂-phenyl | |
| 997 | " | " | " | 2,4,6-(CH₃)₃-phenyl | |
| 998 | " | " | " | 2-CH₃O-phenyl | |
| 999 | " | " | " | 4-CH₃O-phenyl | |
| 1001 | " | " | " | 4-C₂H₅O-phenyl | |
| 1002 | " | " | " | 4-CF₃O-phenyl | |
| 1003 | " | " | " | 4-CN-phenyl | |
| 1004 | " | " | " | 3-NO₂-phenyl | |
| 1005 | " | " | " | 4-NO₂-phenyl | |
| 1006 | F | F | NCOOEt | CH₃ | |
| 1007 | " | " | " | C₂H₅ | |
| 1008 | " | " | " | n-C₃H₇ | |
| 1009 | " | " | " | i-C₃H₇ | |
| 1010 | " | " | " | n-C₄H₉ | |
| 1011 | " | " | " | i-C₄H₉ | |
| 1012 | " | " | " | s-C₄H₉ | |
| 1013 | " | " | " | t-C₄H₉ | |
| 1014 | " | " | " | n-C₆H₁₃ | |
| 1015 | " | " | " | CH₂-t-Bu | |
| 1016 | " | " | " | CF₃ | |
| 1017 | " | " | " | C₂F₅ | |
| 1018 | " | " | " | n-C₃F₇ | |

TABLE 4-continued

Pyrrolines and imidazolines of the formula (I), G = 5-isoxazolinyl

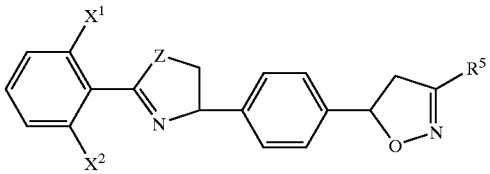

| Ex. No. | X¹ | X² | Z | R⁵ | Physical data |
|---|---|---|---|---|---|
| 1019 | " | " | " | n-C₄F₉ | |
| 1020 | " | " | " | n-C₅F₁₁ | |
| 1021 | " | " | " | n-C₆F₁₃ | |
| 1022 | " | " | " | phenyl | |
| 1023 | " | " | " | 2-F-phenyl | |
| 1024 | " | " | " | 3-F-phenyl | |
| 1025 | " | " | " | 4-F-phenyl | |
| 1026 | " | " | " | 2-Cl-phenyl | |
| 1027 | " | " | " | 3-Cl-phenyl | |
| 1028 | " | " | " | 4-Cl-phenyl | |
| 1029 | " | " | " | 2,4-Cl₂-phenyl | |
| 1030 | " | " | " | 3,4-Cl₂-phenyl | |
| 1031 | " | " | " | 2,5-Cl₂-phenyl | |
| 1032 | " | " | " | 2,6-Cl₂-phenyl | |
| 1033 | " | " | " | 2-CF₃-phenyl | |
| 1034 | " | " | " | 3-CF₃-phenyl | |
| 1035 | " | " | " | 3,5-(CF₃)₂-phenyl | |
| 1036 | " | " | " | 4-CF₃-phenyl | |
| 1037 | " | " | " | 2-CH₃ | |
| 1045 | " | " | " | 4-CF₃O-phenyl | |
| 1046 | " | " | " | 4-CN-phenyl | |
| 1047 | " | " | " | 3-NO₂-phenyl | |
| 1048 | " | " | " | 4-NO₂-phenyl | |

C. FORMULATION EXAMPLES a) A dusting powder is obtained by mixing 10 parts by weight of active compound and 90 parts by weight of talc, as inert substance, and comminuting the mixture in an impact mill.

b) A wettable powder which is readily dispersible in water is obtained by mixing 25 parts by weight of active compound, 65 parts by weight of kaolin-containing quartz, as the inert substance, 10 parts by weight of potassium ligninsulfonate and 1 part by weight of sodium oleoylmethyltaurinate, as wetting and dispersing agent, and grinding the mixture in a pinned disk mill.

c) A dispersion concentrate which is readily dispersible in water is prepared by mixing 40 parts by weight of active compound with 7 parts by weight of a sulfosuccinic monoester, 2 parts by weight of a sodium ligninsulfonate and 51 parts by weight of water and grinding the mixture to a fineness of below 5 microns in a grinding bead mill.

d) An emulsifiable concentrate can be prepared from 15 parts by weight of active compound, 75 parts by weight of cyclohexane, as the solvent, and 10 parts by weight of ethoxylated nonylphenol (10 EO), as the emulsifier.

e) Granules can be prepared from 2 to 15 parts by weight of active compound and an inert granule carrier material, such as attapulgite, pumice granules and/or quartz sand. A suspension of the wettable powder from Example b) having a solids content of 30% is expediently used, and this is sprayed onto the surface of attapulgite granules and the components are dried and mixed intimately. The weight content of the wettable powder is approximately 5% and that of the inert carrier material is approximately 95% of the finished granules.

D. BIOLOGICAL EXAMPLES

EXAMPLE 1

Effect on the Spider Mite Tetranychus Urticae

Cut stems of bean plants (Phaseolus vulgaris) carrying one leaf are transferred into brown glass bottles filled with tap water and subsequently populated with approximately 100 spider mites (Tetranychus urticae). Plant leaf and spider mites are then dipped for 5 seconds. into an aqueous solution of the formulated preparation to be examined. After the solution has run off, plants and animals are stored in a climatized chamber (16 hours of lightday, 25° C., 40–60% relative atmospheric humidity). After 6 days of storage, the mortality of the preparation on all stages of the spider mites is determined. At a concentration of 500 ppm (based on the content of active compound), the preparations of Example Nos. 1, 2, 5, 9,10, 12, 20 22, 23, 32, 33, 35, 39, 41, 42, 43, 45, 46, 48, 49, 52, 63, 76, 79, 87, 90, 91, 92, 95, 96, 97, 99, 108, 110, 113, 117, 120, 569, 570, 573, 574, 576, 578, 579, 589, 600, 605, 619, 623, 624, 625, 626, 628, 629, 630, 631 effect a mortality of 80–100%.

EXAMPLE 2

Effect on the Aphid Aphis Fabae

Cut stems of bean plants (Phaseolus vulgaris) carrying one leaf are transferred into brown glass bottles filled with tap water and subsequently populated with approximately 100 aphids (Aphis fabae). Plant leaf and aphids are then dipped for 5 seconds into an aqueous solution of the formulated preparation to be examined. After the solution has run off, plants and animals are stored in a climatized chamber (16 hours of light/day, 25° C., 40–60% relative atmospheric humidity). After 6 days of storage, the mortality of the preparation on all stages of the aphid is determined. At a concentration of 500 ppm (based on the content of active compound), the preparations of Example Nos. 96 and 103 effect a mortality of 80–100%.

EXAMPLE 3

Effect on the Egg-larval Stage of Heliothis Virescens

A Petri dish whose bottom is covered with filter paper and which contains about 5 ml of nutrient medium is prepared. Filter paper sections containing approximately 30 24-hour-old eggs of the tobacco budworm (Heliothis virescens) are dipped for 5 seconds into an aqueous solution of the formulated preparation to be examined and subsequently placed into the Petri dish. A further 200 □l of the aqueous solution are distributed over the nutrient medium. After the Petri dish has been closed, it is stored in a climatized chamber at about 25° C. After 6 days of storage, the mortality of the preparation on the eggs and any larvae hatched from them is determined. At a concentration of 500 ppm (based on the content of active compound), the preparations of Example Nos. 1, 5, 9, 20, 22, 28, 39, 45, 46, 48, 49, 52, 63, 94, 103, 116, 568, 567, 573, 579, 589, 619, 623 effect a mortality of 80–100%.

EXAMPLE 4

Feeding Effect on the Butterfly Larvae Heliothis Virescens

Nutrient medium (freeze-dried cube) is dipped into an aqueous solution of the formulated preparation to be examined and then placed into a Petri dish. Ten L2 larvae of the tobacco budworm (Heliothis virescens) are then added. The Petri dish is then closed with a lid. The effect of the preparation on the larvae is determined after 4 days of storage at about 23° C. At a concentration of 500 ppm (based on the content of active compound), the preparations of Example Nos. 2, 9, 13, 20, 22, 28, 29, 30, 32, 35, 39, 40, 41, 42, 43, 45, 46, 48, 49, 52, 63, 76, 78, 91, 93, 94, 95, 98, 103, 114, 116, 117, 120, 121, 124, 125, 567, 573, 589, 600, 605, 613, 614, 615, 619, 621, 623, 624, 629 effect a larvae mortality of 80–100%.

EXAMPLE 5

Feeding Effect on the Butterfly Larvae Spodoptera Litoralis

Nutrient medium (freeze-dried cube) is dipped into an aqueous solution of the formulated preparation to be examined and then placed into a Petri dish. Ten L2 larvae of the Egyptian cotton leaf worm (Spodoptera litoralis) are then added. The Petri dish is then closed with a lid. The effect of the preparation on the larvae is determined after 4 days of storage at about 23° C. At a concentration of 500 ppm (based on the content of active compound), the preparations of Example Nos. 5, 9, 12, 28, 29, 30, 35, 39, 40, 41, 42, 43, 45, 46, 48, 52, 63, 87, 90, 91, 92, 94, 97, 98, 99, 100, 103, 107, 113, 117, 120, 125, 566, 567, 573, 574, 589, 600, 613, 614, 619, 626 effect a larvae mortality of 80–100%.

What is claimed is:

1. An arylisoxazoline of the formula (I):

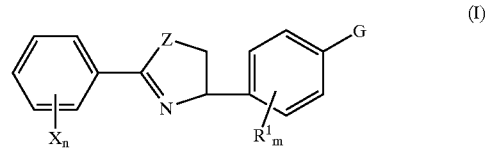

in which:

X is identical or different and is:
  a) halogen, cyano, nitro;
  b) $(C_1-C_4)$-alkyl, $(C_1-C_4)$-alkoxy, $(C_1-C_4)$-alkylthio, or $(C_1-C_4)$-alkylsulfinyl, where the substituents of group b are unsubstituted or substituted by one or more halogen atoms;

$R^1$ is identical or different and is halogen, $(C_1-C_4)$-haloalkyl, $(C_1-C_4)$-alkyl, $(C_1-C_4)$-alkoxy, $(C_1-C_4)$-haloalkoxy or cyano;

m is 0 to 4;

n is 1 to 5;

Z is oxygen, sulfur, $CH_2$ or $NR^2$;

$R^2$ is CN, $C_1-C_4$-alkoxy-$(C_1-C_4)$-alkyl, CHO, $(C_1-C_6)$-alkylcarbonyl, $(C_1-C_6)$-alkoxycarbonyl or (CW) $NR^3R^4$;

$R^3$, $R^4$ are identical or different and are H or $(C_1-C_6)$-alkyl;

W is O or S;

G is mono- to tetrasubstituted isoxazoline

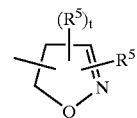

which is attached in the 3-, 4- or 5-position to the adjacent phenyl ring;

t is 0, 1, 2 or 3;

$R^5$ is identical or different and is:
  a) halogen, CN, $NO_2$;
  b) a straight or branched alkyl group having 1 to 12 carbon atoms, where one or more ($CH_2$) groups are optionally replaced by —O—, —S(O)—$_{0,1,2}$, —NH—, —NR—, —CO—, —CS—, —CH=CH—, —C≡C—, unsubstituted or substituted aryldiyl, unsubstituted or substituted heterocyclyldiyl, unsubstituted or substituted ($C_3$–$C_8$)-cycoalkanediyl or unsubstituted or substituted ($C_3$–$C_8$)-cycoalkenediyl, with the proviso that chalcogens when present are not adjacent to one another, where individual hydrogen atoms are optionally replaced by halogen;
  c) in the case of two radicals $R_5$ located in the a-position, the radicals are also (=Y), where Y is (=O), (=S), (=$NOR^6$) or (=$CR_2^6$);

with the proviso that the radical(s) $R^5$ together do not comprise more than one ring system having five or more members; and $R^6$ is ($C_1$–$C_4$)-alkyl, unsubstituted or substituted phenyl or unsubstituted or substituted benzyl;

or a pure optical or geometrical isomer, isomer mixture, N-oxide or salt thereof.

2. A compound as claimed in claim 1, wherein:

X is halogen, cyano, nitro, ($C_1$–$C_4$)-alkyl, ($C_1$–$C_3$)-haloalkyl, ($C_1$–$C_4$)-alkoxy or ($C_1$–$C_3$)-haloalkoxy;

m is 0 or 1;

n is 1, 2 or 3;

Z is oxygen or $CH_2$;

$R^1$ is halogen, ($C_1$–$C_4$)-haloalkyl, ($C_1$–$C_4$)-alkyl, ($C_1$–$C_4$)-alkoxy or ($C_1$–$C_4$)-haloalkoxy;

G is

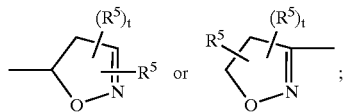

t is 0, 1, 2 or 3;

$R^5$ is identical or different and is:
  a) halogen, CN, $NO_2$; or
  b) a straight-chain or branched alkyl group having 1 to 12 carbon atoms, where one or more ($CH_2$) groups are optionally replaced by —O—, —S(O)—$_{0,1,2}$, —NH—, —NR—, —CO—, —CS—, —CH=CH—, —C≡C—, unsubstituted or substituted aryldiyl, unsubstituted or substituted heterocyclyldiyl, unsubstituted or substituted ($C_3$–$C_8$)-cycloalkanediyl or unsubstituted or substituted ($C_3$–$C_8$)-cycloalkenediyl, with the proviso that chalcogens when present cannot be adjacent to one another, and where individual hydrogen atoms are optionally replaced by halogen;
and when two radicals $R^5$ are located in the α-position, the radicals can also be combined to form (=Y), where Y is (=O), (=S), (=$NOR^6$) or (=$CR_2^6$);

with the proviso that the radical(s) $R^5$ together do not comprise more than one ring system having five or more members; and $R^6$ is ($C_1$–$C_4$)-alkyl, unsubstituted or substituted phenyl or unsubstituted or substituted benzyl.

3. A compound as claimed in claim 2, where the groups $R^5$ are as defined below:

$R^5$ is CN, unsubstituted or substituted phenyl, unsubstituted or substituted phenoxy, ($C_1$–$C_6$)-alkyl, ($C_1$–$C_6$)-alkenyl, ($C_1$–$C_6$)-haloalkyl, ($C_1$–$C_6$)-haloalkenyl, —($C_1$–$C_6$)-alkanediyl-aryl, where the aryl group is unsubstituted or substituted and where one —$CH_2$-unit is optionally replaced by —C(O)—$NR^{10}$—, $NR^{10}$—(CO), $NR^{10}$ or O;

$R^{10}$ is H, ($C_1$–$C_6$)-alkyl, ($C_1$–$C_6$)-haloalkyl, unsubstituted or substituted phenyl, unsubstituted or substituted benzyl.

4. A compound as claimed in claim 1, where

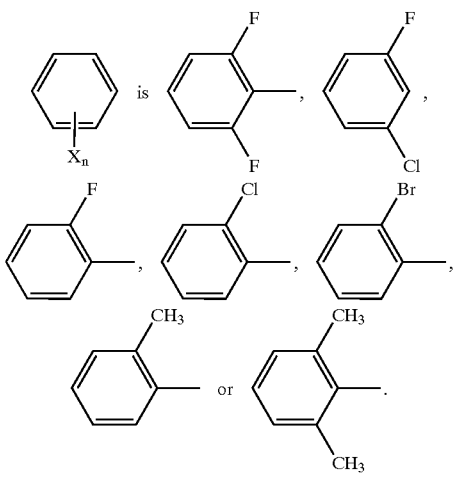

5. A compound as claimed in claim 1, having the formula:

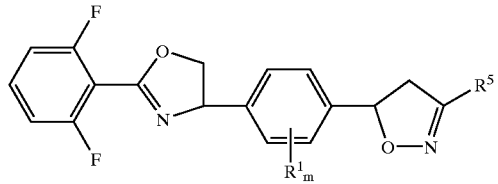

(11)

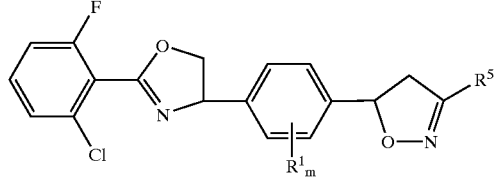

(12)

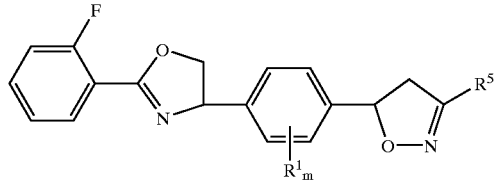

(13)

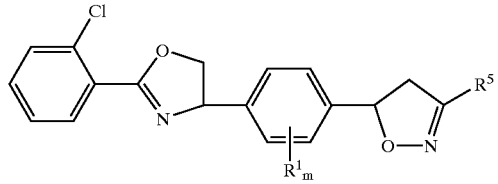

(14)

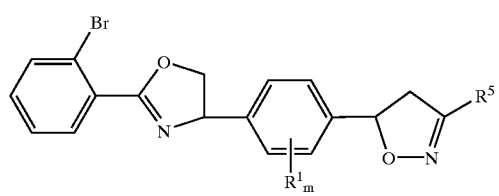
(15)
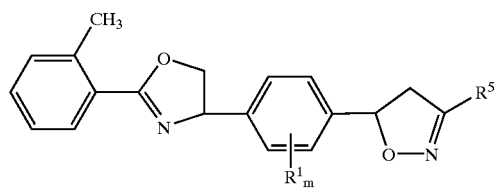
(16)
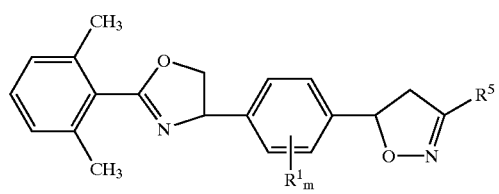
(17)
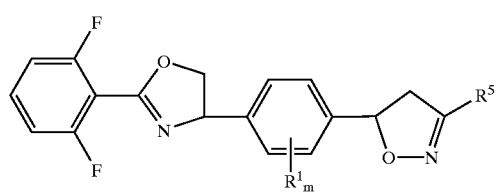
(18)
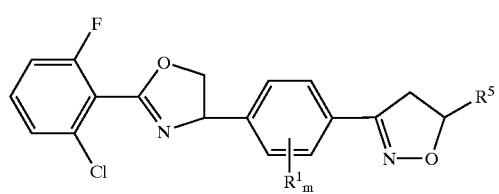
(19)
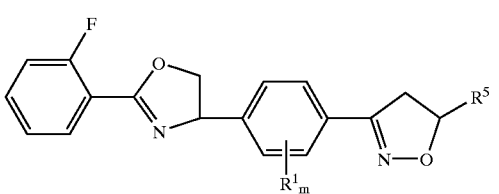
(110)
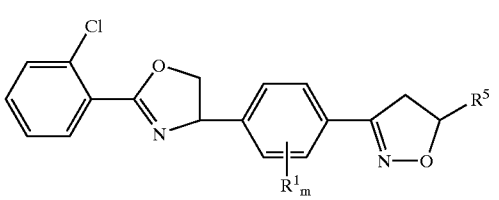
(111)
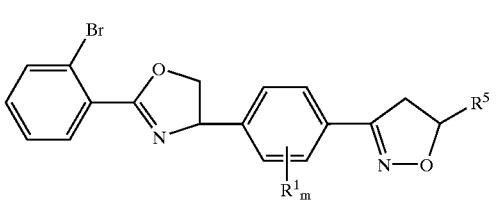
(112)
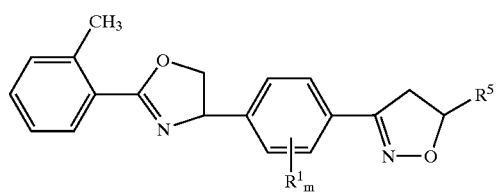
(113)
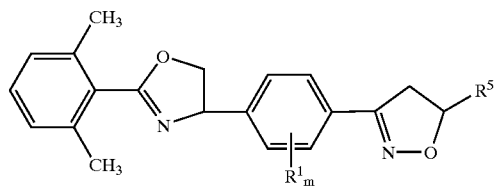
(114)
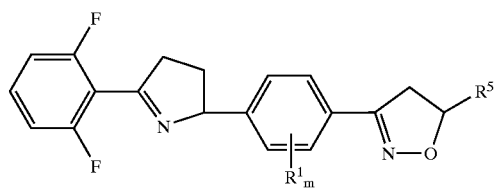
(115)
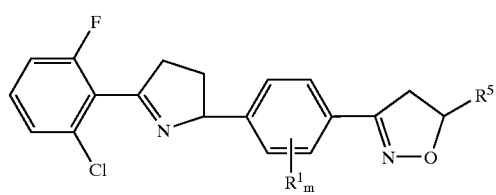
(116)
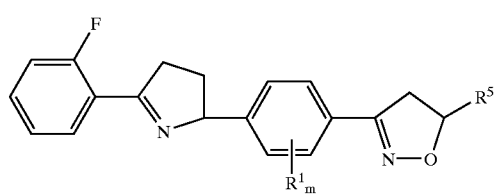
(117)
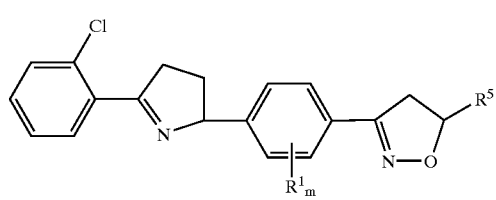
(118)
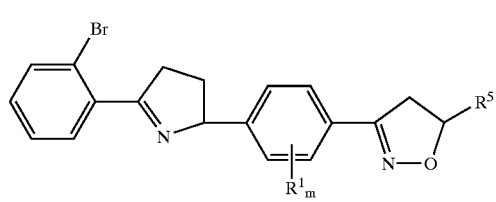
(119)
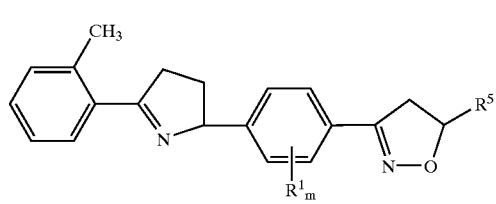
(120)

-continued (121) 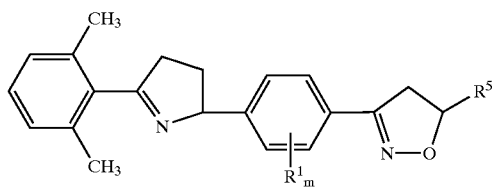

(122) 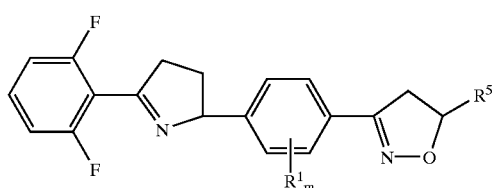

(123) 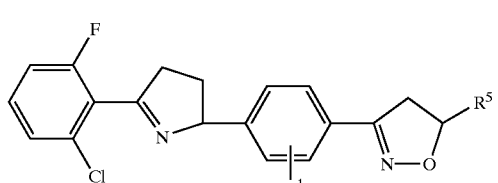

(124) 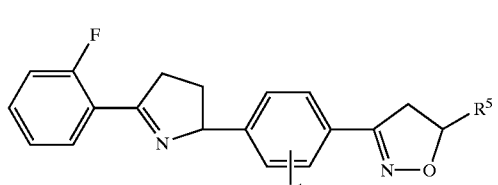

(125) 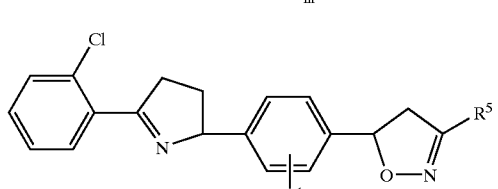

(126) 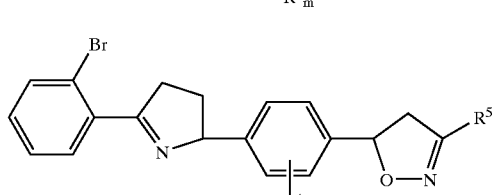

(127) 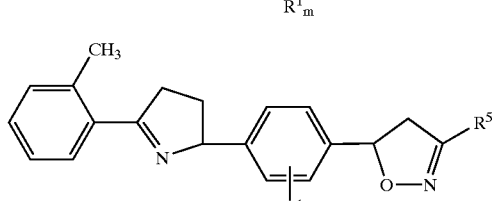

(128) 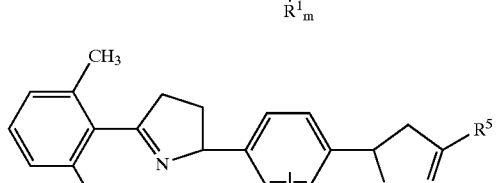

where $R^1$, m and $R^5$ are as defined in claim 1.

6. A process for preparing a compound of the formula (I) as claimed in claim 1, said process comprising:

a) reacting an oxime of the formula (II):

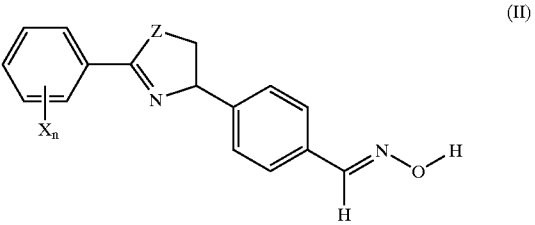

(II)

wherein X and n are as defined in claim 1, with a chlorinating agent to give a compound of the formula (III):

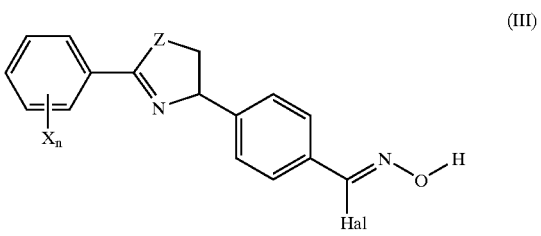

(III)

in which X and n are as defined in claim 1 and Hal is halogen,
and then reacting further with an olefin of the formula (IV):

(IV)

wherein $R^5$ and t are as defined in claim 1, to afford the corresponding compound of formula (I) having a 3-isoxazinyl radical; or b) reacting an olefin of the formula (VII):

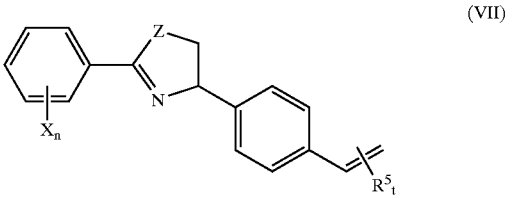

(VII)

wherein X, n, $R^5$ and t are as defined in claim 1, with a halogenated oxime of the formula (VIII):

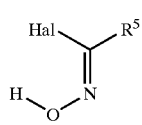

(VIII)

to afford the corresponding compound of formula (I) having a 5-isoxazinyl radical.

7. A pesticidal composition comprising a pesticidally effective amount of at least one compound as claimed in claim 1, and at least one formulation auxiliary.

8. An insecticidal, acaricidal or nematocidal composition comprising an insecticidally, acaricidally or nematocidally effective amount, respectively, of at least one compound as claimed in claim 1, and at least one formulation auxiliary.

9. A pesticidal composition comprising an insecticidally, acaricidally and/or nematocidally effective amount of at least one compound as claimed in claim 1 and at least one further active compound selected from the group consisting of insecticides, attractants, sterilizing agents, acaricides, nematocides, fungicides, molluscides, growth-regulating substances and herbicides and at least one formulation auxiliary.

10. A composition for use in timber protection or as a preservative in sealants, in paints, in cooling lubricants for metal working or in drilling and cutting oils, comprising a pesticidally effective amount of at least one compound as claimed in claim 1 and at least one formulation auxiliary compatible with timber, sealants, paints, cooling lubricants for metal working, drilling oils or cutting oils.

11. A veterinary composition comprising a pesticidally effective amount of at least one compound as claimed in claim 1 and at least one veterinarily acceptable formulation auxiliary.

12. A process for preparing a pesticidal composition comprising a pesticidally effective amount of at least one compound of claim 1 and at least one formulation auxiliary, which comprises combining the compound of claim 1 and at least one formulation auxiliary and formulating them into a suitable formulation.

13. A method for controlling harmful insects, Acarina, molluscs and/or nematodes, comprising contacting insects, Acarina, molluscs and/or nematodes, with an insecticidally, acaricidally, molluscidally or nematocidally effective amount of at least one compound as claimed in claim 1.

14. A method for controlling harmful insects, Acarina, molluscs and/or nematodes, comprising applying to these organisms or to the plants, areas or substrates infested with them an insecticidally, acaricidally, moluscidally and/or nematocidally effective amount of a composition as claimed in claim 7.

15. A seed coated with a pesticidally effective amount of a compound as claimed in claim 1.

16. A seed coated with a pesticidally effective amount of a composition as claimed in claim 7.

17. A compound as claimed in claim 5, wherein:
m is 0 or 1;
$R^1$ is halogen, $(C_1-C_4)$-haloalkyl, $(C_1-C_4)$-alkyl, $(C_1-C_4)$-alkoxy or $(C_1-C_4)$-haloalkoxy; and
$R^5$ is CN, unsubstituted or substituted phenyl, unsubstituted or substituted phenoxy, $(C_1-C_6)$-alkyl, $(C_1-C_6)$-alkenyl, $(C_1-C_6)$-haloalkyl, $(C_1-C_6)$-haloalkenyl, or —$(C_1-C_6)$-alkanediyl-aryl, wherein the aryl group is unsubstituted or substituted and wherein one —$CH_2$— unit is optionally replaced by —C(O)—$NR^{10}$—, $NR^{10}$—(CO), $NR^{10}$ or O; and
$R^{10}$ is H, $(C_1-C_6)$-alkyl, $(C_1-C_6)$-haloalkyl, unsubstituted or substituted phenyl, or unsubstituted or substituted benzyl.

18. The compound having the formula:

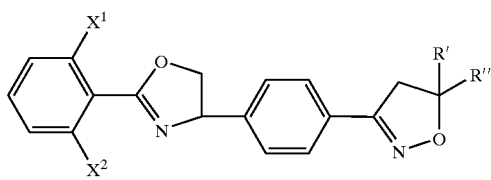

wherein:
(a) $X^1$ is F, $X^2$ is F, R' is H and R" is methyl;
(b) $X^1$ is F, $X^2$ is F, R' is H and R" is isopropyl;
(c) $X^1$ is F, $X^2$ is F, R' is H and R" is tert-butyl;
(d) $X^1$ is F, $X^2$ is F, R' is H and R" is n-hexyl;
(e) $X^1$ is F, $X^2$ is F, R' is H and R" is chloromethyl;
(f) $X^1$ is F, $X^2$ is F, R' is H and R" is bromomethyl;
(g) $X^1$ is F, $X^2$ is F, R' is methyl and R" is tert-butyl;
(h) $X^1$ is F, $X^2$ is F, R' is methyl and R" is $CH_2$-(tert-butyl);
(i) $X^1$ is F, $X^2$ is F, R' is methyl and R" is chloromebthyl;
(j) $X^1$ is F, $X^2$ is F, R' is H and R" is isobutoxy;
(k) $X^1$ is F, $X^2$ is F, R' is H and R" is cyano;
(l) $X^1$ is F, $X^2$ is F, R' is H and R" is ethoxymethyl;
(m) $X^1$ is F, $X^2$ is F, R' is H and R" is n-propoxymethyl;
(n) $X^1$ is F, $X^2$ is F, R' is H and R" is n-butoxymethyl;
(o) $X^1$ is F, $X^2$ is F, R' is H and R" is $CH_2OCF_2CF_2H$;
(p) $X^1$ is F, $X^2$ is F, R' is H and R" is $CH_2OCH_2CF_3$;
(q) $X^1$ is F, $X^2$ is F, R' is H and R" is phenoxymethyl;
(r) $X^1$ is F, $X^2$ is F, R' is H and R" is 2-pyridyloxymethyl;
(s) $X^1$ is F, $X^2$ is F, R' is H and R" is trifluoromethyl;
(t) $X^1$ is F, $X^2$ is F, R' is H and R" is n-$C_3F_7$;
(u) $X^1$ is F, $X^2$ is F, R' is H and R" is n-$C_4F_9$;
(v) $X^1$ is F, $X^2$ is F, R' is H and R" is n-$C_6F_{13}$;
(w) $X^1$ is F, $X^2$ is F, R' is H and R" is phenyl;
(x) $X^1$ is F, $X^2$ is F, R' if H and R" is 4-fluorophenyl;
(y) $X^1$ is F, $X^2$ is F, R' is H and R" is 4-trifluoromethylphenyl;
(z') $X^1$ is F, $X^2$ is F, R' is H and R" is benzyl;
(a') $X^1$ is F, $X^2$ is F, R' is H and R" is $C_2H_4Br$;
(b') $X^1$ is F, $X^2$ is F, R' is H and R" is methylthiomethyl;
(c') $X^1$ is F, $X^2$ is F, R' is H and R" is $COOC_2H_4CF_3$;
(d') $X^1$ is F, $X^2$ is F, R' is H and R" is $CONHC_2H_5$;
(e') $X^1$ is F, $X^2$ is F, R' is H and R" is $CON(CH_3)_2$;
(f') $X^1$ is F, $X^2$ is F, R' is H and R" is $CON(C_2H_5)_2$;
(g') $X^1$ is F, $X^2$ is F, R' is H and R" is $CONH(n-C_3H_7)$;
(h') $X^1$ is F, $X^2$ is F, R' is H and R" is $CONHCH_2C_2F_5$;
(i') $X^1$ is F, $X^2$ is F, R' is H and R" is $CONHCH_2C_2H_3$;
(j') $X^1$ is F, $X^2$ is F, R' is H and R" is CONH(tert-butyl);
(k') $X^1$ is F, $X^2$ is F, R' is H and R" is CONH-(n-pentyl);
(l') $X^1$ is F, $X^2$ is F, R' is H and R" is $CONHC_3H_6OCH_3$;
(m') $X^1$ is F, $X^2$ is F, R' is H and R" is $CONHCH_2C_3F_7$;
(n') $X^1$ is F, $X^2$ is F, R' is H and R" is $CONHCH_2$-(2-tetrahydrofuranyl);
(o') $X^1$ is F, $X^2$ is F, R' is H and R" is CONH(4-trifluoromethylphenyl);
(p') $X^1$ is F, $X^2$ is F, R' is H and R" is $CONHC_2H_4$(1-piperidinyl);
(q') $X^1$ is F, $X^2$ is F, R' is H and R" is $CONHCH_2CF_3$;
(r') $X^1$ is F, $X^2$ is F, R' is H and R" is $CONHCH_2$-(2,6-difluorophenyl);
(s') $X^1$ is F, $X^2$ is F, R' is H and R" is $CONHCH_2$-(3-trifluoromethylphenyl);
(t') $X^1$ is F, $X^2$ is F, R' is H and R" is $CH_2NHCOCH_3$;
(u') $X^1$ is F, $X^2$ is F, R' is H and R" is $CH_2NHCOC_2H_5$;
(v') $X^1$ is F, $X^2$ is F, R' is H and R" is $CH_2NHCOC_2F_5$;
(w') $X^1$ is F, $X^2$ is F, R' is H and R" is $CH_2NHCO$-n-propyl;
(x') $X^1$ is F, $X^2$ is F, R' is H and R" is $CH_2NHCOC_2H_4CF_3$;
(y') $X^1$ is F, $X^2$ is F, R' is H and R" is $CH_2NHCO$(4-chlorophenyl); or (z′) $X^1$ is F, $X^2$ is F, R′ is H and R″ is $CH_2NHCO$(2-chloro-5-pyridyl).

19. The compound having the formula:

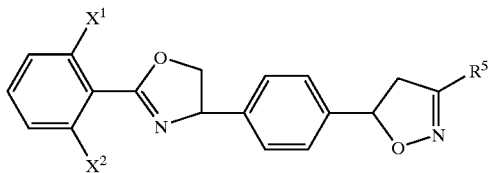

wherein:
(a) $X^1$ is F, $X^2$ is F and $R^5$ is methyl;
(b) $X^1$ is F, $X^2$ is F and $R^5$ is ethyl;
(c) $X^1$ is F, $X^2$ is F and $R^5$ is n-propyl;
(d) $X^1$ is F, $X^2$ is F and $R^5$ is isopropyl;
(e) $X^1$ is F, $X^2$ is F and $R^5$ is n-butyl;
(f) $X^1$ is F, $X^2$ is F and $R^5$ is tert-butyl;
(g) $X^1$ is F, $X^2$ is F and $R^5$ is n-pentyl;
(h) $X^1$ is F, $X^2$ is F and $R^5$ is $CH(C_2H_5)_2$;
(i) $X^1$ is F, $X^2$ is F and $R^5$ is $CH_2CF_3$;
(j) $X^1$ is F, $X^2$ is F and $R^5$ is $C_2H_4CF_3$;
(k) $X^1$ is F, $X^2$ is F and $R^5$ is 4-fluorophenyl;
(l) $X^1$ is F, $X^2$ is F and $R^5$ is 4-trifluoromethylphenyl;
(m) $X^1$ is F, $X^2$ is F and $R^5$ is 2,4,6-trimethylphenyl;
(n) $X^1$ is F, $X^2$ is F and $R^5$ is COOH;
(o) $X^1$ is F, $X^2$ is F and $R^5$ s $COOC_2H_5$;
(p) $X^1$ is F, $X^2$ is F and $R^5$ is $COOCH_2CF_3$;
(q) $X^1$ is F, $X^2$ is F and $R^5$ is $CONHC_2H_5$;
(r) $X^1$ is F, $X^2$ is F and $R^5$ is $CON(C_2R_5)_2$;
(s) $X^1$ is F, $X^2$ is F and $R^5$ is $CONHCH_2C_2F_5$;
(t) $X^1$ is F, $X^2$ is F and $R^5$ is CONH-(tert-butyl);
(u) $X^1$ is F, $X^2$ is F and $R^5$ is $CONHCH_2C_2H_3$;
(v) $X^1$ is F, $X^2$ is F and $R^5$ is $CONHCH_2C_3F_7$;
(w) $X^1$ is F, $X^2$ is F and $R^5$ is $CONHCH_2CF_3$;
(x) $X^1$ is F, $X^2$ is F and $R^5$ is $CONHC_3H_6OCH_3$;
(y) $X^1$ is F, $X^2$ is F and $R^5$ is $CONHCH_2$-(2-tetrahydrofuranyl); or
(z) $X^1$ is F, $X^2$ is F and $R^5$ is $CONHCH_2$-(2,6-difluorophenyl).

20. A veterinary composition as claimed in claim 11, wherein said amount of said at least one compound is an amount effective to control endo- or ectoparasites.

* * * * *